United States Patent
Gura et al.

(10) Patent No.: US 7,854,718 B2
(45) Date of Patent: Dec. 21, 2010

(54) DUAL-VENTRICLE PUMP CARTRIDGE, PUMP AND METHOD OF USE IN A WEARABLE CONTINUOUS RENAL REPLACEMENT THERAPY DEVICE

(75) Inventors: Victor Gura, Beverly Hills, CA (US); Edmond Rambod, Los Angeles, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 631 days.

(21) Appl. No.: 11/500,572

(22) Filed: Aug. 7, 2006

(65) Prior Publication Data

US 2007/0060786 A1 Mar. 15, 2007

Related U.S. Application Data

(63) Continuation-in-part of application No. 10/940,862, filed on Sep. 14, 2004, now Pat. No. 7,309,323, which is a continuation-in-part of application No. 10/085,349, filed on Nov. 16, 2001, now Pat. No. 6,960,179.

(51) Int. Cl.
*A61M 37/00* (2006.01)
*C02F 1/44* (2006.01)

(52) U.S. Cl. .................. 604/6.1; 604/6.11; 604/5.01; 604/5.04; 604/4.01; 210/645; 210/646

(58) Field of Classification Search ............... 604/4.01, 604/5.01, 5.04, 6.09, 6.1, 6.11; 210/645, 210/646, 743, 433.1
See application file for complete search history.

(56) References Cited

U.S. PATENT DOCUMENTS

| | | | |
|---|---|---|---|
| 3,388,803 A | 6/1968 | Scott | |
| 3,746,175 A | 7/1973 | Markley | |
| 3,884,808 A | 5/1975 | Scott | |
| 3,989,622 A | 11/1976 | Marantz et al. | |
| 3,994,799 A | 11/1976 | Yao et al. | |
| 4,094,775 A | 6/1978 | Mueller | |
| 4,212,738 A | 7/1980 | Henne | |
| 4,247,393 A | 1/1981 | Wallace | |
| 4,267,040 A | 5/1981 | Schal | |
| 4,269,708 A | 5/1981 | Bonomini et al. | |
| 4,326,955 A * | 4/1982 | Babb et al. | 210/638 |
| 4,443,333 A | 4/1984 | Mahurkar | |
| 4,765,907 A | 8/1988 | Scott | |
| 4,897,189 A | 1/1990 | Greenwood et al. | |
| 4,997,570 A | 3/1991 | Polaschegg | |
| 5,284,470 A | 2/1994 | Beltz | |
| 5,415,532 A | 5/1995 | Loughnane et al. | |
| 5,577,891 A * | 11/1996 | Loughnane et al. | 417/53 |
| 5,672,268 A * | 9/1997 | Mizrahi et al. | 210/110 |

(Continued)

OTHER PUBLICATIONS

Shettigar, et al, "A portable hemodialysis/hemofiltration system independent of dialysate and infusion fluid." Artif Organs, vol. 7, No. 2, May 1983, pp. 254-256.

(Continued)

*Primary Examiner*—Leslie R Deak
(74) *Attorney, Agent, or Firm*—Hamilton, Brook, Smith & Reynolds, P.C.

(57) ABSTRACT

A dual channel pulsatile pump for use with a completely wearable renal replacement device is provided.

10 Claims, 22 Drawing Sheets

U.S. PATENT DOCUMENTS

| | | | |
|---|---|---|---|
| 5,902,336 | A | 5/1999 | Mishkin |
| 5,944,684 | A | 8/1999 | Roberts et al. |
| 5,980,481 | A | 11/1999 | Gorsuch |
| 5,984,891 | A | 11/1999 | Keilman et al. |
| 6,117,100 | A | 9/2000 | Powers et al. |
| 6,117,122 | A | 9/2000 | Din et al. |
| 6,196,922 | B1 | 3/2001 | Hantschk et al. |
| 6,406,631 | B1 | 6/2002 | Collins et al. |
| 6,610,036 | B2 * | 8/2003 | Branch et al. .............. 604/295 |
| 6,796,955 | B2 | 9/2004 | O'Mahony et al. |

OTHER PUBLICATIONS

Manns, Markus et al, "The acu-men: A New Device for Continuous Renal Replacement Therapy in Acute Renal Failure," Kidney International, vol. 54, 1998, pp. 268-274.

Lockridge, R.S. Jr., "The Direction of End-Stage Renal Disease Reimbursement in the United States," Semin Dial, vol. 17, 2004, pp. 125-130.

Lockridge, R.S. Jr., et al, "Is HCFA's Reimbursement Policy Controlling Quality of Care for End-State Renal Disease Patients?" ASAIO J, vol. 47, 2001, pp. 466-468.

Manns, B.J. et al, "Dialysis Adequacy and Health Related Quality of Life in Hemodialysis Patients," ASAIO J, vol. 48, 2002, pp. 565-569.

Mapes, D.L. et al, "Health-related Quality of Life as a Predictor of Mortality and Hospitalization: The Dialysis Outcomes and Practice Patterns Study (DOPPS)," Kidney Int., vol. 64, 2003, pp. 339-349.

McFarlane, P.A. et al, "The Quality of Life and Cost Utility of Home Nocturnal and Conventional In-center Hemodialysis," Kidney Int., vol. 64, 2003, pp. 1004-1011.

Mohr, P. E., et al, "The Case for Daily Dialysis: Its Impact on Costs and Quality of Life," Am J Kidney Dis., vol. 37, 2001, pp. 777-789.

Patel, S. S., et al, "Psychosocial Variables, Quality of Life, and Religious Beliefs in ESRD Patients Treated with Hemodialysis," Am J Kidney Dis., vol. 40, 2002, pp. 1013-1022.

"Sorbent Dialysis Primer," Organon Teknika Corp., 1991.

Ronco, C., et al, "Blood and Dialysate Flow Distribution in Hollow-fiber Hemodialyzers Analyzed by Computerized Helical Scanning Technique," J Am Soc Nephrol, vol 13, 2002, pp. S53-S61.

Mineshima, M., et al, "Effects of Internal Filtration on the Solute Removal Efficiency of a Dialyzer." ASAIO J, vol. 46, 2000, pp. 456-460.

Ronco, C., et al, "The Hemodialysis System: Basic Mechanisms of Water And Solute Transport in Extracorporeal Renal Replacement Therapies," Nephrol Dial Transplant, vol. 13 Suppl. 6, 1998, pp. 3-9.

Miwa, M. et al, "Push/Pull Hemodiafiltration: Technical Aspects and Clinical Effectiveness," Artif Organs, vol. 23, 1999, pp. 1123-1128.

Runge, T.M., et al, "Hemodialysis: Evidence of Enhanced Molecular Clearance and Ultrafiltration Volume By Using Pulsatile Flow," Int J Artif Organs, vol. 16, 1993, pp. 645-652.

Ding, L. H., et al, "Dynamic filtration of Blood: A New Concept for Enhancing Plasma Filtration," Int J Artif Organs, vol. 14, 1991, pp. 365-370.

Bird, R. B., et al, Transport Phenomena, Wiley, New York, 1976, pp. 126-130, 502-531, 558-563, 624-625, 700-711.

Welty, J. R., et al, "Chapter 27: Unsteady-state Molecular Diffusion," Fundamentals of Momentum, Heat, and Mass Transfer (2nd ed.), McGraw-Hill, New York, 1984.

Siaghy, E. M., et al, "Consequences of Static and Pulsatile on Transmembrane Exchanges During Vitro Microdialysis: Implication for Studies in Cardiac Physiology," Med Biol Eng Comput, vol. 37, 1999, pp. 196-201.

Utsunomiya, T., et al, "Effect of Direct Pulsatile Peritoneal Dialysis on Peritoneal Permeability and Lymphatic Absorption in the Rat," Nippon Jinzo Gakkai Shi, vol. 37, 1995, pp. 24-28.

Jaffrin, M. Y., et al, "Rationale of Filtration Enhancement in Membrane Plasmapheresis by Pulsatile Blood Flow," Life Support Systems, vol. 5, 1987, pp. 267-271.

Kobayashi, E., "A Study of Inorganic Ion Exchangers VII; The Synthesis of gammaNH4ZrH(PO4)2 and Ion-Exchange Properties of gamma-NH4Zr(HPO4)2.2H20," Bull Chem Soc Jpn, vol. 56, 1983, pp. 3756-3760.

Suri, R, et al, "Adequacy of Quotidian Hemodialysis," Am J Kidney Dis, vol. 42 Suppl. 1, 2003, pp. S42-S48.

Gotch, F. A., "The Current Place of Urea Kinetic Modelling with Respect to Different Dialysis Modalities," Nephrol Dial Transplant, vol. 13 Suppl. 6, 1998, pp. 10-14.

Gotch, F. A., et al, "Effective Diffusion Volume Flow Rates (Qe) for Urea, Creatinine, and Inorganic Phosphorous (Qeu, Qecr, QeiP) During Hemodialysis," Semin Dial, vol. 16, 2003, pp. 474-476.

Roberts, Martin, "Wearable Artificial Kidneys for Continuous Dialysis," ASAIO Journal, 1993, pp. 19-23.

Murisasco, A., et al, "Continuous Arterio-venous Hemofiltration in a Wearable Device to Treat End-stage Renal Disease," Trans Am Soc Artif Intern Organs, 1986, vol. XXXII, pp. 567-571.

Murisasco, A., et al, "A Continuous Hemofiltration System Using Sorbents for Hemofiltrate Regeneration," Clinical Nephrology, 1986, pp. S53-S57, vol. 26, Supp. No. 1.

Lande', Arnold J., et al, "In Search of a 24 Hours Per Day Artificial Kidney," Journal of Dialysis, 1(8), 1977, pp. 805-823.

Gura, V., et al, "CRRT for ESRD: The Wearable Artificial Kidney: A Feasible, Safe, and Cost Effective Way to Provide Daily Dialysis," J Am Soc Nephrol, vol. 15, 2004, p. 639A.

\* cited by examiner

DUAL-VENTRICLE PUMP CARTRIDGE, PUMP AND METHOD OF USE IN A WEARABLE CONTINUOUS RENAL REPLACEMENT THERAPY DEVICE

REFERENCE TO RELATED APPLICATIONS

This application is a continuation-in-part of U.S. patent application Ser. No. 10/940,862, filed Sep. 14, 2004, which is a continuation-in-part of U.S. patent application Ser. No. 10/085,349, filed Nov. 16, 2001, all which are hereby incorporated by reference. This application also claims priority from U.S. Provisional Patent Application No. 60/706,167, filed Aug. 5, 2005, which is incorporated herein by reference.

BACKGROUND OF THE INVENTION

The present invention is related to a pump for a dialysis system, and more particularly to a pump and method of using the pump with a completely wearable dialysis or hemodiafiltration system. Furthermore, the present invention relates to a dual channel pulsatile pump cartridge and more particularly, to a method and apparatus for valving a the dual channel pulsatile pump cartridge that provides secure open/close valving and variable half-cycle fluid flow between channels.

Hemodialysis is a process by which microscopic toxins are removed from the blood using a filtering membrane such as a dialyzer. Typically, hemodialysis is administered in intermittent three to four hours sessions, which take place two or three times per week. The outcomes of renal replacement therapy in the form of hemodialysis remain dismal regarding the quality of life, morbidity and mortality of these unfortunate patients. A growing body of literature and research that indicates that daily dialysis may be conducive to numerous biochemical and clinical improvements as well as in quality of life and potentially increased longevity of end-stage renal disease patients. However, the implementation of daily dialysis is almost impossible due to manpower and cost constraints. Furthermore, Continuous Renal Replacement Therapy (CRRT) over intermittent dialysis since far more toxins can be removed from the blood using CRRT seven days a week, twenty-four hours a day. Some advantages of CRRT include an expected decrease rate of morbidity and mortality, a decrease in the amount of medications required, a decrease in fluid intake and dietary restrictions, and numerous improvements in the quality of life of the ESRD patients Existing CRRT machines are large, heavy machines adapted to provide around the clock dialysis, hemofiltration or a combination of both to individual patients. The existing CRRT machines are cumbersome and must be hooked to electrical outlets and several feet of tubing. In addition, these machines require a continuous supply of gallons of fresh water to create dialysate fluid. Further, a patient must remain connected to the existing heavy and cumbersome CRRT machine for many hours, limiting his or her ability to perform normal every day activities.

An additional problem with existing dialysis machines, is that frequent reconnection to the machine requires accessing blood flow by puncturing an arteriovenous shunt. These shunts only last for limited periods of time and are subject to infection, clotting and other complications that result in numerous hospitalizations and repeated surgical interventions.

On the other hand, implementation of daily dialysis encounters obstacles that make its accomplishment in a large scale practically impossible. Some of these obstacles include the inability or unwillingness of most patients to dialyze at home, the lack of manpower both in nurses and technicians to provide more treatments in the dialysis units, and the reluctance of governmental payers to shoulder the expense of additional procedures. Also, its implementation would not only take time, but major capital investments are required to build additional capacity in dialysis units. Although home dialysis might be the answer to the problem, most patients are unable or unwilling to use home dialysis machines. Thus, the need for a technological solution that will allow for increased dialysis time without incurring additional costs or necessitating additional manpower.

Continuous renal replacement therapy (CRRT) allows significantly higher doses of dialysis, but is unsuitable for treating End-Stage Renal Disease (ESRD) patients because the machines are heavy, attached to a wall electrical outlet and require many gallons of water.

Unsuccessful attempts have been made to create a prescription or a commercially available wearable dialysis device or Wearable Artificial Kidney (WAK) that can provide CRRT. Because of the bulky nature of typical dialyzers and associated sorbent devices, the concept of a wearable dialysis device or WAK has yet to become a reality for dialysis patients. In view of the above disadvantages, there continues to be a substantial need for a portable, wearable CRRT device, which can be used substantially continually, 24 hours a day, seven days a week. There is also a need for improved subsystems, such as pumps, sensors and the like, that can be incorporated into a WAK so that the WAK can truly operate as a CRRT device.

SUMMARY OF THE INVENTION

One embodiment of the present invention involves a dual channel pulsatile pump comprising a dual channel pump cartridge having a first channel and a second channel, each channel of said dual channel pump cartridge comprising a peristaltic tube that is compressible, said peristaltic tube has an input end and an output end. An input valve is at the input end, said input valve comprises an input o-ring, an input ball that seats against said input o-ring to stop fluid back flow through said input valve and an input spring member that positions said input ball against said input o-ring when the peristaltic tube is being compressed, said input spring member allows said input ball to move away from said input o-ring and allow forward fluid flow through said input valve when said peristaltic tube is being allowed to decompress. There is an output valve at said output end, said output valve comprises an output o-ring, an output ball that seats against said output o-ring to stop fluid back flow through said output valve and an output spring member that positions said output ball against said output o-ring when the peristaltic tube is being decompressed, said output spring member allows said output ball to move away from said output o-ring and allow forward fluid flow through said output valve when said peristaltic tube is being compressed. Also included in an exemplary embodiment is a pump motor portion comprising a first oscillating pushing member for compressing and decompressing said peristaltic tube in a first channel and a second oscillating pushing member for compressing and decompressing said peristaltic tube in a second channel, said dual channel pump cartridge being removably attachable to said pump motor portion.

Further applicability of embodiments of the present invention will become apparent from a review of the detailed description and accompanying drawings. It should be understood that the description and examples, while indicating embodiments of the present invention, are not intended to limit the scope of the invention, and various changes and modifications within the spirit and scope of the invention will become apparent to those skilled in the art.

BRIEF DESCRIPTION OF THE DRAWINGS

The present invention will become more fully understood from the detailed description given below, together with the accompanying drawings, which are given by way of illustration only, and are not to be construed as limiting the scope of the present invention. In the drawings.

DETAILED DESCRIPTION OF THE PREFERRED EMBODIMENTS

Figure 1:
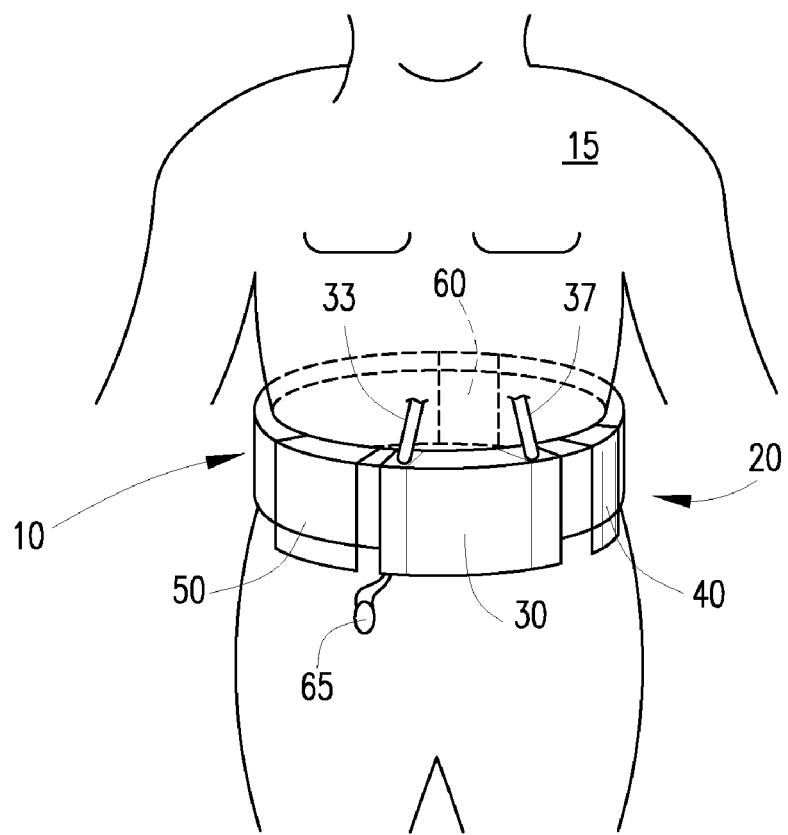
FIG. 1 is a perspective view of the wearable CRRT device worn around the waist of a dialysis patient according to the present invention.
Figure 2:
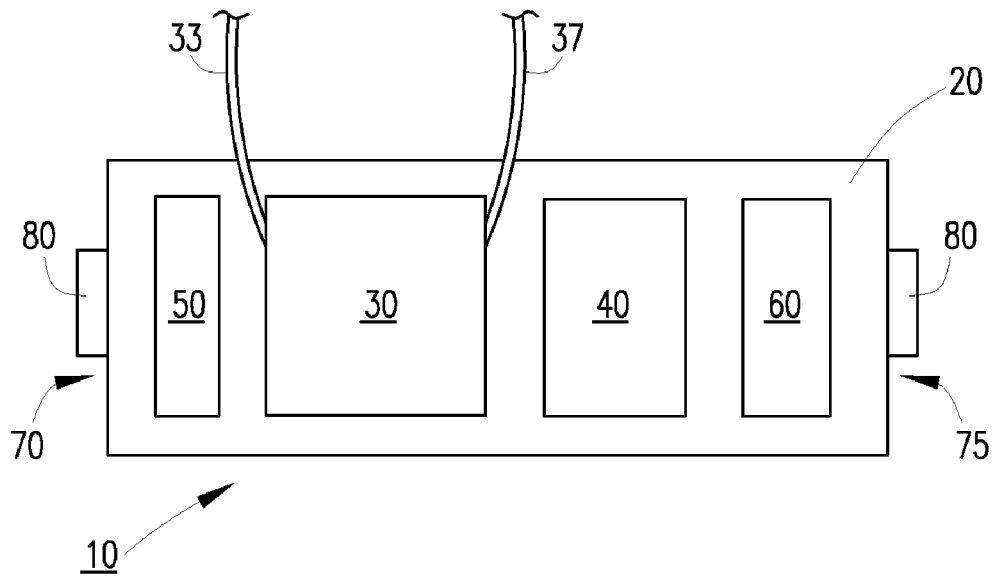
FIG. 2 is a front view of the wearable CRRT device of FIG. 1 after being detached from the dialysis patient.

Referring to FIGS. 1 and 2, a continuous renal replacement therapy (CRRT) device 10 is adapted to be worn about a portion of the body of a dialysis patient 15. The CRRT device 10 includes a belt 20 that is divided into a number of sections comprising: a dialyzer section 30 including a blood inlet tube 33 leading from a blood vessel and a blood outlet tube leading to a blood vessel; a sorbent section 40; an additive pump section 50; and an electronic control section 60, which includes a microprocessor and batteries to power device 10.

As best seen in FIG. 2, the belt 20 includes a pair of end portions 70, 75, which are secured together by a conventional belt fastener 80 such as a buckle, snaps, buttons or hook and loop fasteners. Although the CRRT device 10 depicted in FIG. 1 is worn about the waist of the patient 15, it should be understood to those of ordinary skill in the art that the device 10 may, alternatively, be worn about other portions of the patient's body, such as over a shoulder of the patient, for example.

Figure 3:
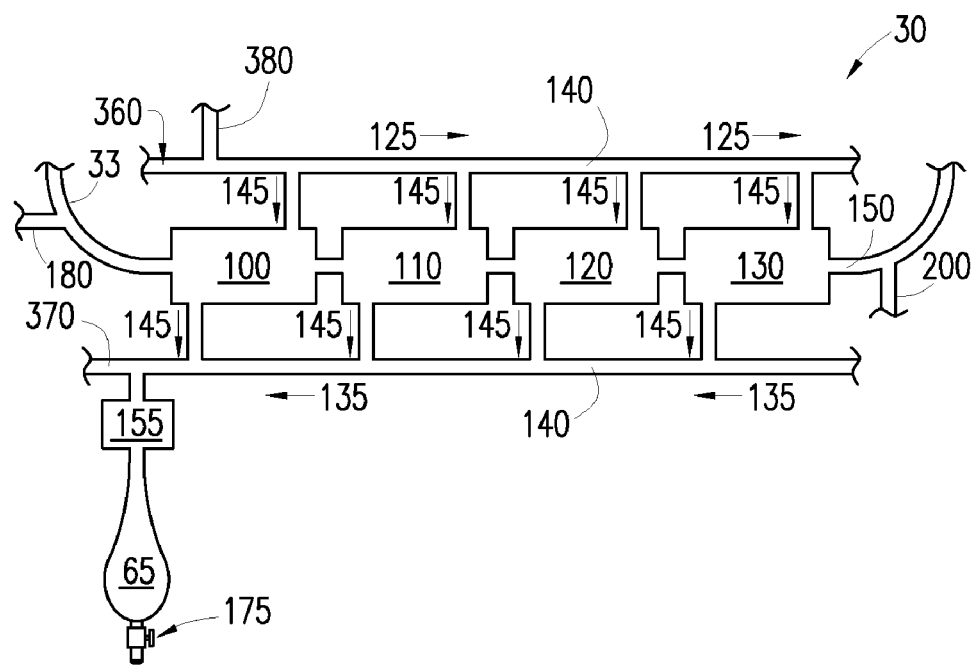
FIG. 3 is a perspective view of the dialyzer section of the wearable CRRT device according to the present invention.

Referring to FIG. 3, the dialyzer section 30 of the belt 20 includes a plurality of miniaturized dialyzers 100, 110, 120, 130 that utilize dialysate fluid 140 to remove impurities from the blood 150 of the patient 15. The number of dialyzers 100, 110, 120, 130 in the plurality of dialyzers 100, 110, 120, 130 may be varied to reflect different dialysis prescriptions. As best seen in FIG. 3, the plurality of dialyzers 100, 110, 120, 130 are connected in series, whereby a conventional pump forces the patient's blood 150 through a blood inlet tube 33, through the dialyzers 100, 110, 120, 130 and into blood outlet tube 37. It should be understood to those of ordinary skill in the art that the dialyzers 100, 110, 120, 130 could also be connected in parallel without departing from the scope of the invention.

During dialysis, the dialysate is pumped in the opposite direction of the blood flow using a conventional pump (not shown) as indicated by arrows 125, 135, 145. Spent dialysate 140 flows toward sorbent section 40 through spent dialysate tube 370. Excess fluid is removed from the spent dialysate 140 through a volumetric 155 and into a waste receiver 65, which is to be periodically emptied by the patient via tap 175. A microprocessor in the electronic section 60 determines the rate and amount of fluid removal through volumetric pump 155.

Figure 4:
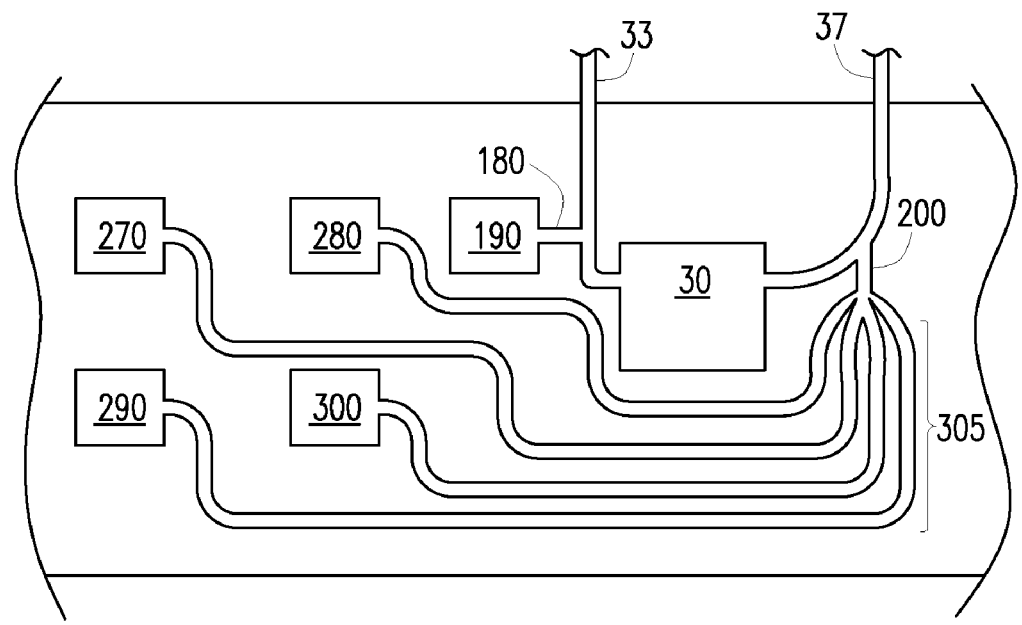
FIG. 4 is a perspective view of the additive pump and dialyzer sections of the wearable CRRT device according to the present invention.

With further reference to FIG. 3, the blood inlet tube 33 includes a side port 180 through which anticoagulant is pumped into the blood by anticoagulant pump 190. Typical anticoagulants are infused into the blood 150 include, but are not limited to, heparin, prostacyclin, low molecular weight heparin, hirudin and sodium citrate. As best seen in FIG. 4, the blood outlet tube 37 includes a side port 200 for the infusion of additives, which are forced into the blood 150 from a plurality of additive pumps 270, 280, 290, 300. Piston, suction, piezo, micro, or very small roller pumps can be employed for this purpose. Such pumps may all be classified as micropumps. Each additive pump 270, 280, 290, 300 forces a controlled amount of respective additive into the blood 150, wherein the rate of infusion of each additive is controlled electronically by the microprocessor in the electronic control section 60. In a known manner, a physician can use the electronic control section 60 to set the rate of infusion for each additive to correspond to a predetermined dose for each additive. Since the additives cannot be mixed together prior to infusion in the blood 150, they have separate circuits 305. Typical additives include, but are not limited to, sodium citrate, calcium, potassium and sodium bicarbonate.

Figure 5:
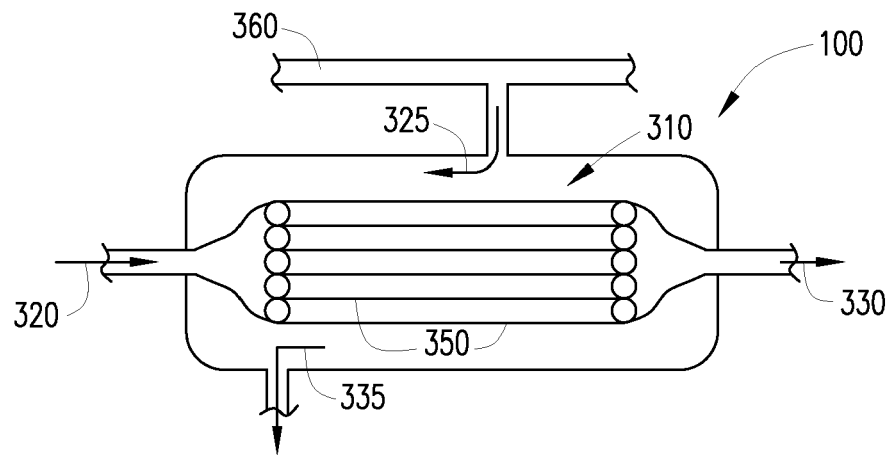
FIG. 5 is a cross-sectional view of a first embodiment of a dialyzer of the wearable CRRT device according to the present invention.
Figure 6:
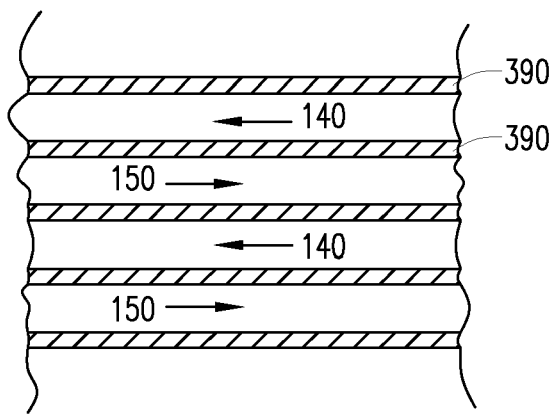
FIG. 6 is a cross-sectional view of a second embodiment of a dialyzer of the wearable CRRT device according to the present invention.

Referring to FIG. 5, in a first dialyzer embodiment, each dialyzer 100, 110, 120, 130 is a conventional dialyzer comprising a plurality of cylindrical hollow fibers 310 through which the blood 150 is circulated. As indicated by arrows 320, 330, the dialysate fluid 140 is circulated around exterior walls 350 of the hollow fibers 310 in a direction across the blood flow inside the hollow fibers 310 as indicated by arrows 325, 335. The exterior walls 350 of the hollow fibers 310 are semiporous so that impurities can be moved from the blood 150 and into the dialysate 140. Fresh dialysate 140 flows from the sorbent section 40 through a dialysate inlet tube 360 and into the series of dialyzers 100, 110, 120, 130. The spent dialysate 140 then flows out of the series of dialyzers 100, 110, 120, 130, through a spent dialysate outlet tube 370 and into the sorbent section 40. The dialysate inlet tube 360 includes a side port 380 (shown in FIG. 3) for the infusion of additives, which can be forced into the blood 150 via the aforementioned additive pumps 270, 280, 290, 300, whereby the rate of infusion is controlled electronically by the microprocessor in the electronic control section 60. Referring to FIG. 6, in second dialyzer embodiment, each dialyzer 100, 110, 120, 130 comprises a plurality of parallel sheets 390 of semiporous material, wherein the dialysate fluid 140 is circulated on one side of the parallel sheets 390 and the blood 150 circulates in the direction on the other side of the parallel sheets 390.

Figure 7:
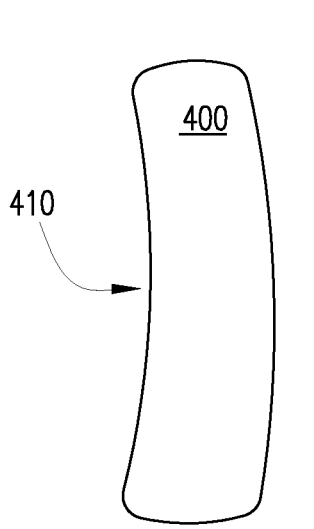
FIG. 7 is a top view of a casing of a dialyzer of the wearable CRRT device according to the present invention.

Referring to FIG. 7, each dialyzer 100, 110, 120, 130 is a miniature dialyzer having a flexible casing 400 adapted to conform to the body contour of the patient. In addition, the body-side wall 410 of each casing 400 is concave to further correspond to bodily curves of the user. The casing 400 can, be made of any suitable material having adequate flexibility for conformance to the portion of the body to which it is applied. Suitable materials include, but are not limited to, polyurethane and poly vinyl chloride.

Figure 8:
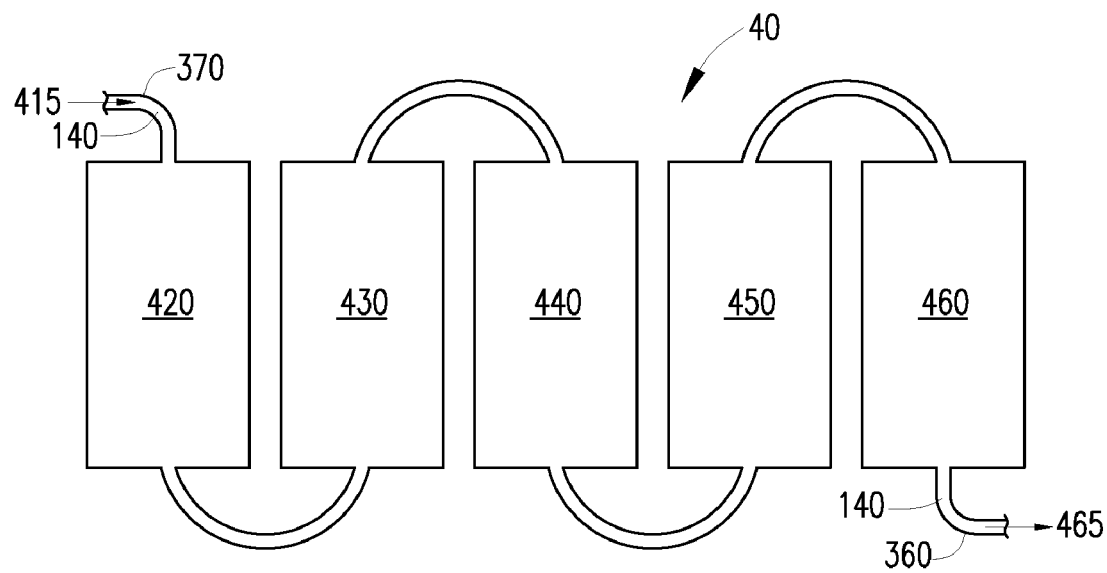
FIG. 8 is a perspective view of a first embodiment of the sorbent section of the wearable CRRT device according to the present invention.
Figure 9:
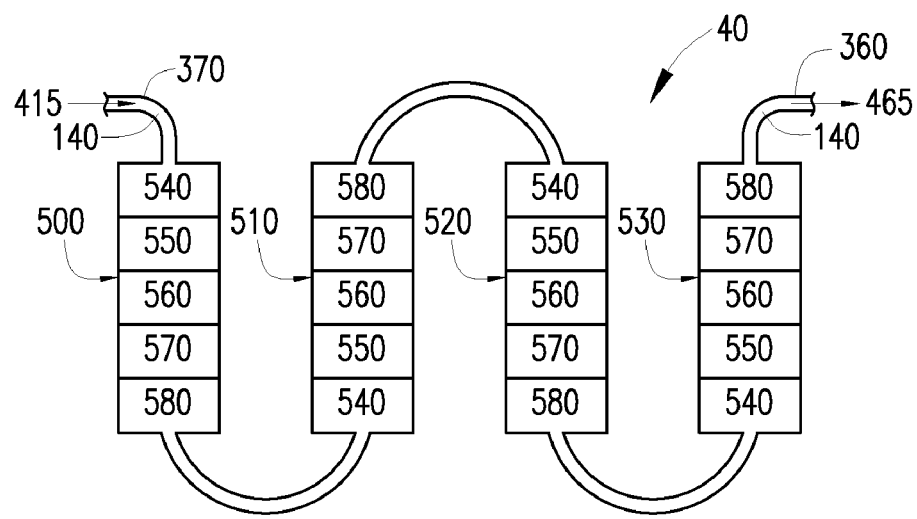
FIG. 9 is a perspective view of a second embodiment of the sorbent section of the wearable CRRT device according to the present invention.
Figure 10:
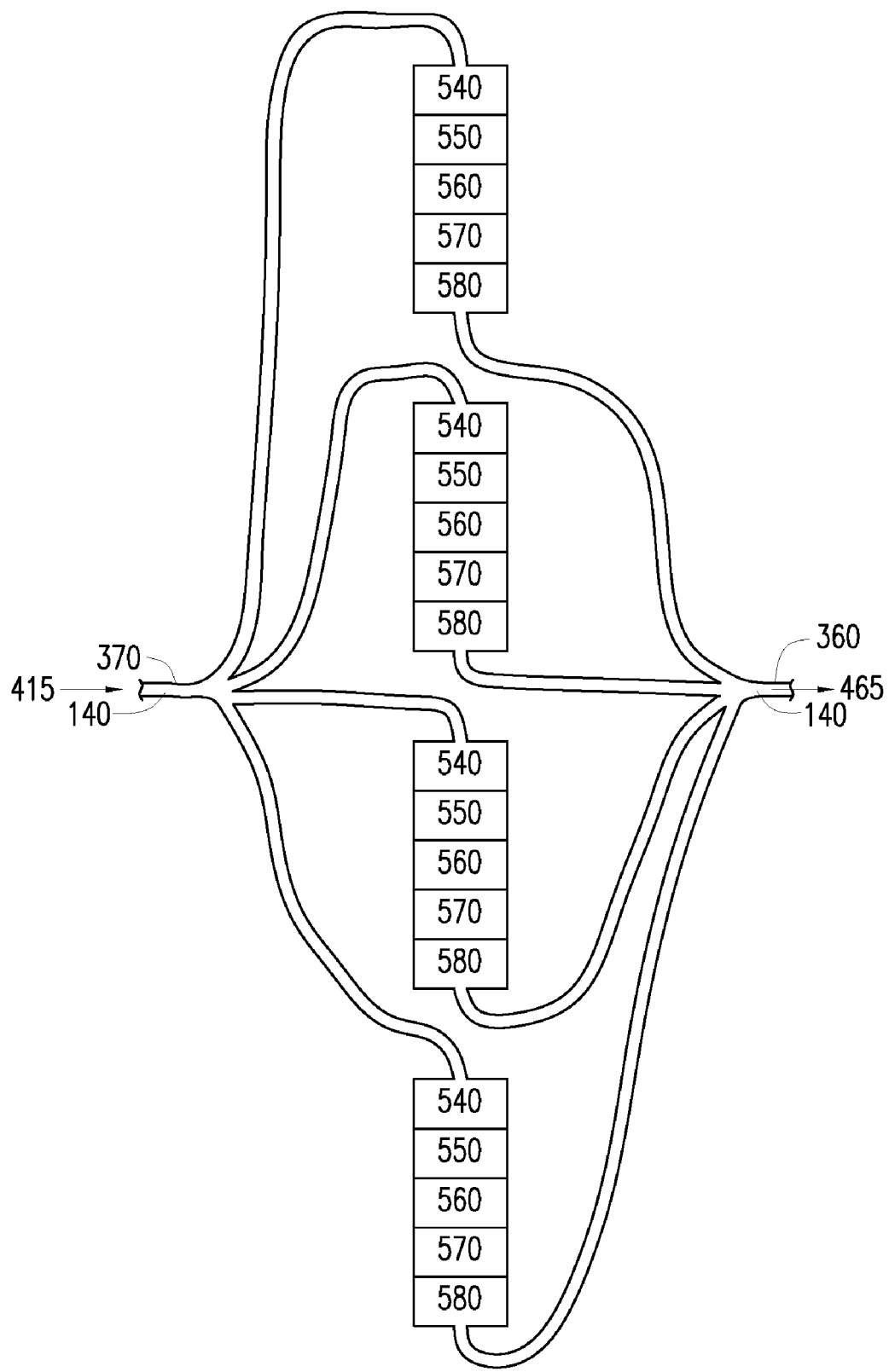
FIG. 10 is a perspective view of a variation of the second embodiment of the sorbent section of the wearable CRRT device according to the present invention.

Referring to FIG. 8-10, in the sorbent section 40, as indicated by arrow 415, spent dialysate 140 flows from the dialyzer section 30 through spent dialysate tube 370 and into a plurality of sorbent devices 420, 430, 440, 450, 460. As indicated by arrow 465, the regenerated dialysate 140 then flows through tube 360 and back into the dialyzer section 30. Preferably, the sorbent devices 420, 430, 440, 450, 460 comprise a series of sorbent cartridges 420, 430, 440, 450, 460 for regenerating the spent dialysate 140. By regenerating the dialysate with sorbent cartridges 420, 430, 440, 450, 460, the exemplary CRRT device 10 requires only a small fraction of the amount of dialysate of a single-pass hemodialysis device. Importantly, each sorbent cartridge 420, 430, 440, 450, 460 is a miniaturized sorbent cartridge 420, 430, 440, 450, 460 containing a distinct sorbent.

Referring to FIG. 8, in a first embodiment of the sorbent section 40, there are five sorbent cartridges 420, 430, 440, 450, 460 including an activated charcoal cartridge 420, a urease cartridge 430, a zirconium phosphate cartridge 440, a hydrous zirconium oxide cartridge 450 and an activated carbon cartridge 460. Those of ordinary skill in the art will recognize that these sorbents are similar to the sorbents employed by the commercially available Recirculating Dialysis (REDY) System. However, in the REDY System, the sorbents are layers of a single cartridge. By contrast, the sorbents of the present invention are each part of a distinct sorbent cartridge 420, 430, 440, 450, 460 such that each cartridge 420, 430, 440, 450, 460 may, conveniently, be replaced and disposed of independently of the other cartridges 420, 430, 440, 450, 460 if so desired. As one of ordinary skill in the art would understand, activated charcoal, urease, zirconium phosphate, hydrous zirconium oxide and activated carbon are not the only chemicals that could be used as sorbents in the present CRRT device 10. In fact, any number of additional or alternative sorbents could be employed without departing from the scope of the present invention.

Referring to FIGS. 9 and 10, in a second embodiment of the sorbent section 40, there are a plurality of sorbent cartridges 500, 510, 520, 530, wherein each cartridge 500, 510, 520, 530 includes a plurality of sorbent layers 540, 550, 560, 570, 580: an activated charcoal layer 540, a urease layer 550, a zirconium phosphate layer 560, a hydrous zirconium oxide layer 570 and an activated carbon layer 580. The cartridges 500, 510, 520, 530 may be in series as depicted in FIG. 9 or may be in parallel as depicted in FIG. 10. In this embodiment, the number of sorbent devices may be varied to correspond with different dialysis prescriptions.

Figure 11:
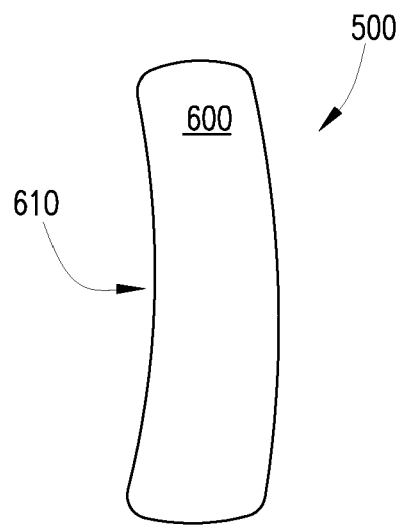
FIG. 11 is a top view of a casing of a sorbent device of the wearable CRRT device according to the present invention.

Referring to FIG. 11, each cartridge 500, 510, 520, 530 is a miniature cartridge having a flexible or curved casing 600 adapted to conform to the body contour of the patient. In addition, the body-side wall 610 of each casing 600 is concave to further correspond to bodily curves. The casing 600 can be made of any suitable material having adequate flexibility for conformance to the portion of the body to which it is applied. Suitable materials include, but are not limited to, polyurethane and poly vinyl chloride.

Figure 12:
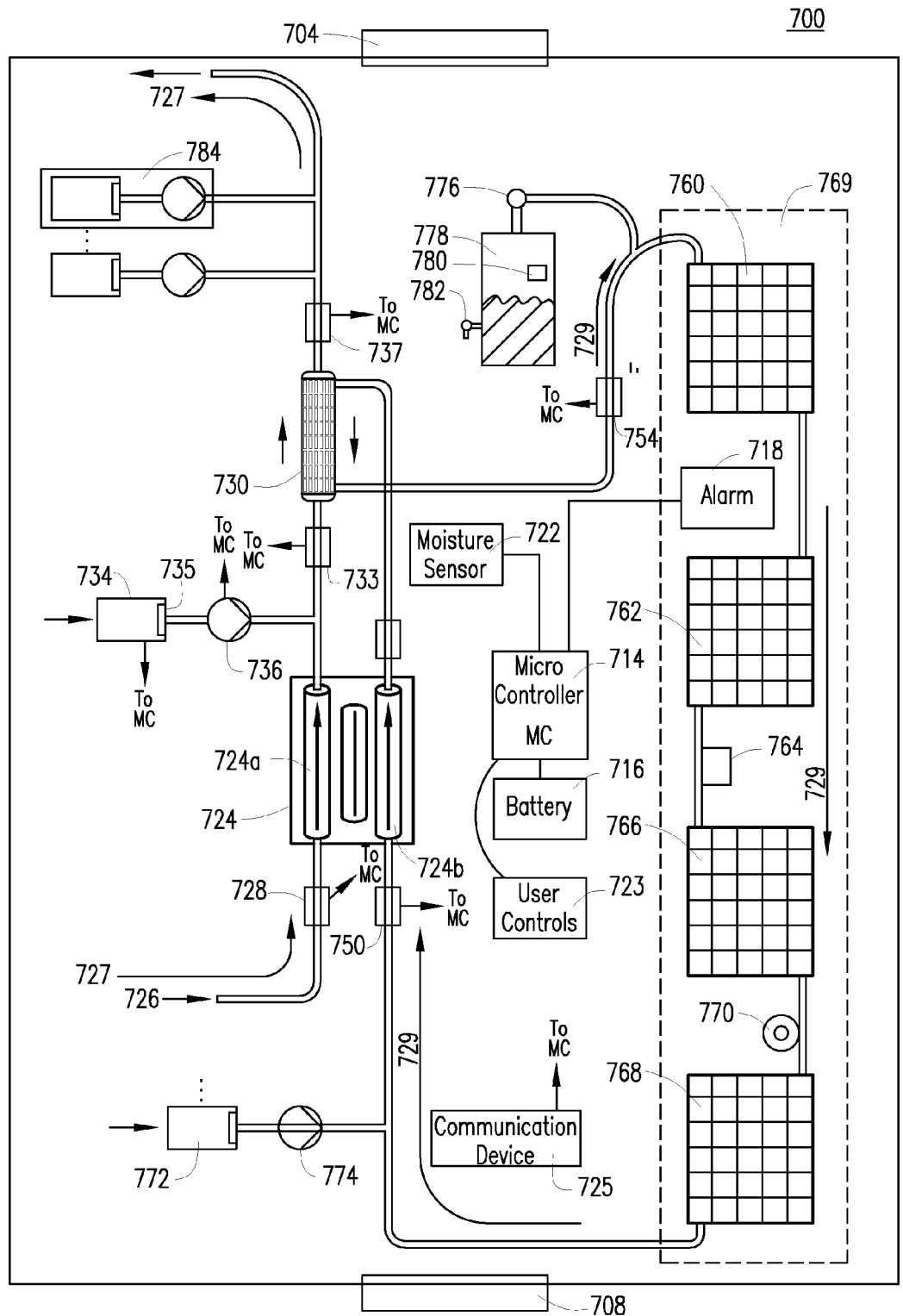
FIG. 12 is a diagram of an exemplary embodiment of the wearable CRRT device.

Referring to FIG. 12, another exemplary embodiment of a wearable CRRT device is depicted. The wearable CRRT device 700 is built into, or is part of, a patient wearable strap, belt or other wearable apparatus 702. The belt 702 may include a pair of endportions 704, 708 that are adapted to be secured together by a fastening means (not specifically shown). The endportion/fastening means 704, 708 could be any number of fastening devices suitable to secure the ends of the belt or strap together, but not limited to snaps, button, buckles, clips, laces, hook and loops, zippers, clasps, etc. An embodiment of a CRRT device may be envisioned to be the shape of an ammunition or military style supply belt, it could also be the shape of a waist-pack. An exemplary wearable CRRT device 700 is worn by a patient either over or under other clothing.

A microcontroller 714 is utilized to control and monitor various aspects of the wearable CRRT device 700. The microcontroller 714 is preferably a low or very low power microcontroller, but may be substantially any microcontroller adapted to operate in an exemplary wearable CRRT device 700. One of the many functions of the microcontroller 714 has is to monitor the battery 716. An exemplary CRRT device 700 will operate continuously for at least 5 to 10 hours using less than 10 continuous watts of power. And preferably less than 3 continuous watts of power. Embodiments of the invention weight less than 10 lbs and preferably less than 5 lbs when operating.

The battery 716 is removably installed in the wearable CRRT device 700. The battery 716 is rechargeable and may be recharged while remaining in the wearable CRRT device 700 via a charging device (not shown) or when disconnected from the wearable CRRT device 700. Preferably the battery 716 can store enough energy to power a wearable CRRT device 700 for at least five (5) or more hours of continuous uninterrupted device operation. The microcontroller, by itself, or via additional circuitry, monitors the charge status of the battery 716. If the microcontroller 714 determines that the battery 716 is low on charge or has less than an estimated predetermined amount of operating time left (e.g., one hour left), the microcontroller 714 may trigger an alarm condition via alarm circuit 718. Alarm circuit 718 may provide any combination of an audio, visual, or physical alarm. The physical alarm signal may include vibrations or small tingle-style shocks to the patient. An alarm condition or warning may be displayed on the display 720 using liquid crystal, light emitting diode or other low power display technology. An alarm condition may also shut down all or predetermined parts of an exemplary wearable CRRT device 700.

A moisture sensor 722 is also in electrical communication with the microcontroller 714. The moisture sensor 722 is used to detect high humidity, condensation, or liquid present inside the packaging or covering over (not specifically shown) the wearable CRRT device 700. The packaging or covering over an exemplary CRRT device 700 may be a plastic, cloth, rubberized, poly-product, or other suitable material. The covering may cover a portion of the wearable CRRT device 700 and allow access to various parts of the device such as the display 720 and user/doctor controls 723.

High humidity, condensation or the presence of liquid inside a wearable CRRT device 700 may be indicative of patient blood leakage, dialysate leakage or other fluid leakage. Upon sensing moisture, the moisture sensor 722 provides a signal to the microcontroller 714 and an alarm is triggered via the alarm circuit 718. Furthermore, the pump 724 may be turned off by the microcontroller 714 to help minimize further blood, dialysate or other fluid loss. The microcontroller may shut down the micropumps (to be discussed later) also. The microcontroller 714 may also prompt an onboard communication device 725 to contact medical help or another entity for medical assistance. The communication device may comprise a paging wireless phone or other mobile communication circuitry. The communication device 725 may also be able to provide the geographic location of the exemplary wearable CRRT device 700.

The pump 724 is an electric pump. The pump 724 may be two pumps 724a and 724b. The two pumps 724a and 724b may each operate off the same or separate electric motors. The pumps 724a and b are powered by the rechargeable battery 716. Furthermore, the microcontroller 714 can be used to adjust various pumping variables. Potential adjustable pumping variables include, but are not limited to, adjusting the pump stroke, volume-per-stroke, speed, torque, pumping rate (i.e., number of pump cycles per minute), pump pressure, pump pressure differential between the input and output of the pump, and pump pause and cycle times.

An exemplary wearable CRRT device 700 has two fluid circuits: a blood circuit 727 and a dialysate circuit 729. A dual channel pulsatile pump 724 may be used in an exemplary embodiment. A pulsatile pump, in general, has a rubberized cartridge for each channel. A cartridge has an input valve at an input side of the cartridge and an output valve at an output end of the cartridge. FIG. 12 depicts a single direction, dual pulsatile pump 724. A dual direction, dual pulsatile pump may also be utilized. A dual direction channel pump is preferred in order to decrease bending of the tubing used in the fluid circuits.

The motor and transmission within the pulsatile pump presses the rubberized, tubular portion of the cartridge. The pressing of the cartridge squeezes and evacuates the contents of the cartridge out of the output valve. As the pump motor spins and causes the mechanics of the pump to release pressure from the rubberized portion of the cartridge, the output valve closes and the input valve opens to allow fluid (blood or dialysate) to enter the cartridge so that the fluid can be squeezed out the output valve in the next pump cycle. The input and output valves are one-way valves allowing fluid flow in a single direction through the cartridge. Other configurations of a pulsatile pump are also available. An exemplary pump 724a, 724b provides a blood flow rate of between about 15 to 100 ml/min (pulsatile). The approximate dimensions of an exemplary dual-pulsatile pump 724 is 9.7×7.1×4.6 cm with a weight of less than 400 grams. The approximate dimensions of a dual channel pump cartridge are 0.72 inches high, 3.82 inches long, and 1.7 inches wide. Exemplary embodiments can be plus or minus 50% of any one or more of these dimension measurements.

An exemplary pulsatile pump uses less than 10 watts of energy and may provide a low battery power and a pump occlusion alarm signal to the microcontroller 714. A lower power pulsatile pump using 5 or less watts may also be used.

The pulsatile pump can be tuned such that the pulses, or cycles, of the two pulse chambers are in phase, 180° out of phase or any predetermined number of degrees out of phase in order to utilize the pulses of the pump to aid in maximizing the dialysis process occurring in the dialyzer 730. The opposite directional flows of blood and dialysate through the dialysate may become more efficient at different phase settings of the pumps 724a and b.

Figure 14:
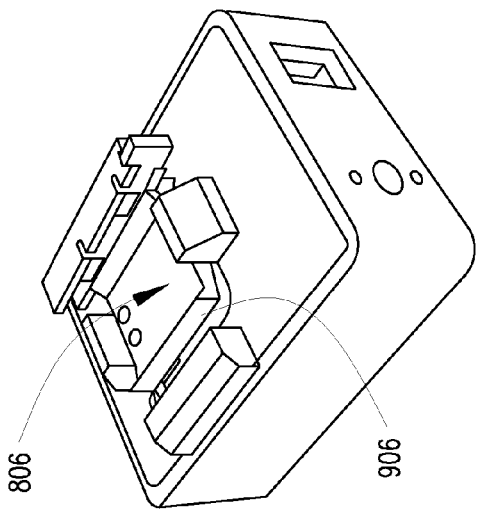
FIG. 14 is an oblique view of an exemplary pump-motor portion of an exemplary dual chamber pulsatile pump.
Figure 13:
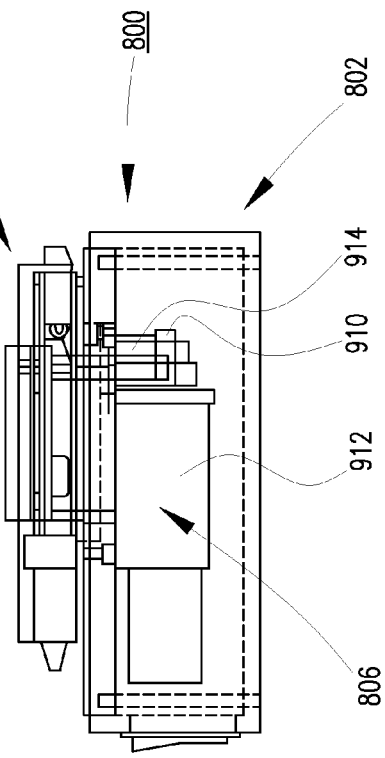
FIG. 13 is a side view of an exemplary dual channel pulsatile pump.
Figure 13B:
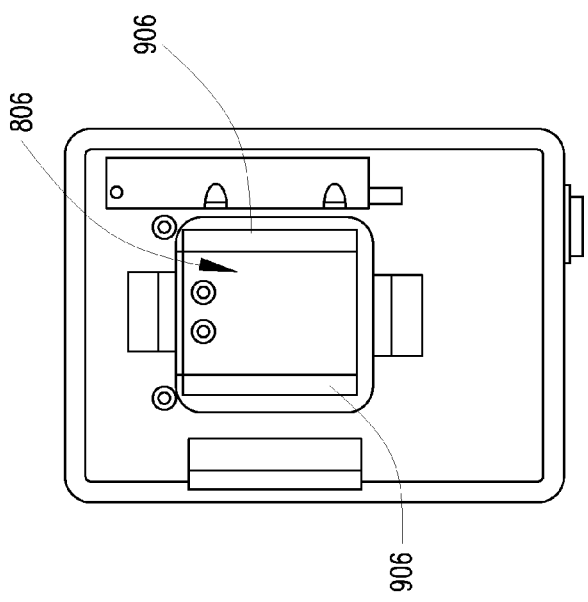
FIGS. 13A and 13B are front and top views of an exemplary pump-motor portion of an exemplary dual chamber pulsatile pump.
Figure 13A:
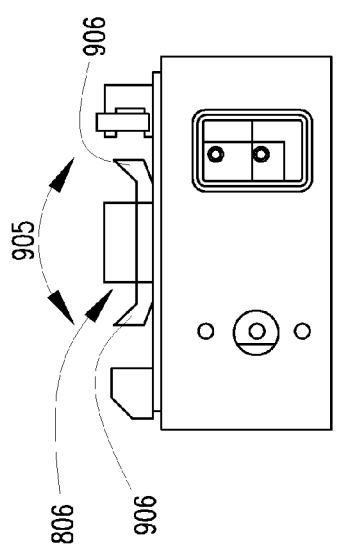
Figure 15:
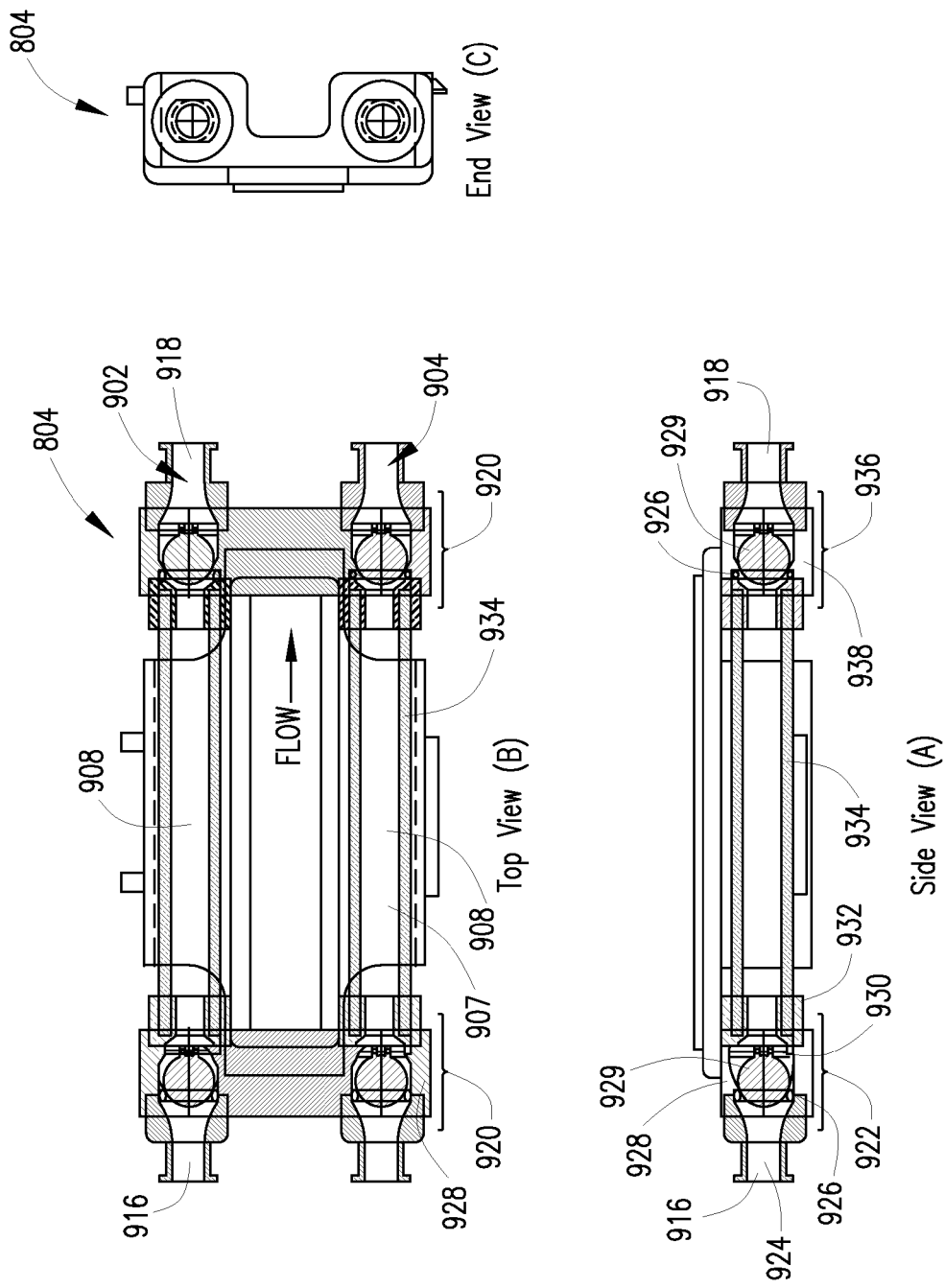
FIG. 15 is a three view of an exemplary dual channel pulsatile pump cartridge.

Referring to FIGS. 13, 14, and 15, wherein FIG. 13 depicts a side view of an exemplary dual-ventricle or dual channel pulsatile pump 800. The dual channel pulsatile pump may comprise at least two distinct components; the pump-motor portion 802 and the dual channel pump cartridge 804. FIGS. 13A and 13B provide an exemplary front and top view of only the pump-motor portion 802. FIG. 14 provides and isometric view the exemplary pump-motor portion 802. FIG. 15 provides a three-view (side A, top B and end C views) of an exemplary dual channel pump cartridge 804. An exemplary dual channel pump cartridge 804 has two members, which provide concurrently synchronized pulsatile movement of one or two distinct liquids. This removable and passive dual channel pump cartridge 804 is constructed to fit within the structure of the dual channel pulsatile pump 800 in a manner that allows the mechanical pump elements 806 of the pump-motor portion 802 to expand and contract a ventricular pumping element 907 in a rhythmic fashion, thereby drawing liquid(s) into the flexible chamber 908 and then pushing it out the other end of the chamber. The exemplary dual channel pump cartridge 804 has a degree of isolation from the pump-motor portion 802. In a two ventricle or dual channel embodiment, the dual channel pump cartridge 804 produces a flow of a first liquid in a first half cycle and a flow of a second liquid in a second half cycle. For example, blood flow may be pumped from a first channel 902 in the first half cycle and dialysate may be pumped from the second channel 904 in the second half cycle.

The actuation of the two chambers of the removable cartridge 804 is done by the oscillation 905 (see arrows in FIG. 13A) of the mechanical pump portion's pushing mechanism 906, which are connected to an output shaft 910 of a fixed or variable speed motor 912 through a driving linkage 914 capable of converting the rotary motion of the output shaft 910 into the oscillating motion 905 of the pushing mechanism 906. The rotary motion of the pump output shaft 910 is caused by a gearing arrangement, which generates both circular and non-circular movements. This combination of motor-driven pushing mechanism 906 and the dual channel pump cartridge 804 may be powered by a variety of power sources, including batteries, DC power or AC power.

The dual channels 902, 904 of the removable cartridge 804 may be configured in such a way as to provide the same or opposite flow directions of the two liquids. FIG. 5 depicts the flow of both channels 902, 904 being in the same direction. One of the channels can manufactured in a flipped or turned around fashion such that the cartridge 804 pumps fluids in opposite directions through channel 902 and channel 904. Each channel 902 and 904 of the removable cartridge 804 has a release mechanism 920 at a channel's input 916 and output 918 that regulates flow direction depending on the configuration. The release mechanism 920, may be a type of one-way valve that is configured in such a manner as to allow fluid flow in one direction if positive pressure is applied or in another configuration only allow flow if negative pressure is applied. An exemplary release mechanism 920 is shown, which may include an occluder-holder combination (discussed in more detail below) that is configured in such a manner as to allow flow in one direction if positive pressure is applied. Embodiments of the exemplary removable cartridge may be comprised of biocompatible materials. The fluid flow regulation is done substantially independent of the density, viscosity and physical properties of the flowing liquids. When used to pump blood, the removable cartridge has low hemolytic characteristics.

An exemplary fluid pump-motor portion 802 has multiple or a single pumping member(s) 906, which provides concurrently synchronized pulsatile movement of one or more distinct and separate fluids in each of the cartridge's channels. Utilizing a pumping chamber 908, in each channel of the dual channel pump cartridge 804, a degree of isolation from the mechanical pump elements 806 is achieved. The removable portion 804 of the dual channel pulsatile pump 800 is constructed to fit within the structure of the pump-motor portion 802 in a manner that allows the mechanical pushing mechanism 906 to expand and contract a ventricular pumping element 907 in a rhythmic fashion, thereby drawing fluid into the input side 916 the flexible pump chamber 908 and then pushing the fluid out the output end 918 of the chamber. In a two chamber embodiment shown, this mechanism produces a flow of a first fluid during a first half cycle and a flow of a second fluid during a second half cycle. Again, for example, blood flow in the first half cycle and dialysate flow in the second half cycle.

In another embodiment of the pump-motor portion 802, the mechanical pump member are connected to the output shaft of a fixed or variable speed, reversible or non-reversible motor through a driving linkage that is a derivation of a crank shaft (not specifically shown) and is capable of translating rotary motion of the output shaft 910 into the oscillating motion of pushing mechanism. This exemplary arrangement comprises both circular and non-circular movements.

In other embodiments of the pump-motor portion the oscillation action of the pushing mechanisms may be tuned such that pushing does not occur only at alternating half cycles or 180 degrees out of phase. Instead, the dual-pushing mechanisms 906 may be adjustable or configured to push or compress the first and second channel's flexible chamber at times that are anywhere from being in-phase (i.e., at the same time) to being 180 degrees out of phase (i.e., at alternating half cycles).

In an experiment using an embodiment of the present invention an exemplary dual channel pulsatile pump 800 was used. This custom-made, battery or converted AC to DC powered pump could have been the mechanical engine of a an exemplary wearable renal replacement device according to various embodiments of the present invention and was responsible for providing simultaneous pulsatile fluid flows of both blood and dialysate through an exemplary renal replacement therapy device. The dual channel pulsatile pump 800 comprised two parts, a micro-motor portion 802 and a flow cartridge 804, as follows:

The 3-Watt DC Micro-Motor: The specifications of this motor are listed below:

| | | |
|---|---|---|
| ☐ | Manufacturer:: | FAULHABER, Germany (Represented by MicroMo, Inc., Florida, USA) |
| ☐ | Part Number: | 1331012S |
| ☐ | Voltage: | 12 Volt nominal |
| ☐ | Terminal Resistant: | 13.3 Ω |
| ☐ | Output Power: | 2.62 Watt |
| ☐ | Efficiency: | 77% |
| ☐ | Speed up to: | 12,000 RPM |
| ☐ | Torque up to: | 0.354 oz-in |
| ☐ | Current up to: | 0.300 Amp |
| ☐ | Gear Head: | 15/5 |
| ☐ | Estimated life-span: | 3,000 hours in continuous operation (according to manufacturer) |

The Dual-Channel Flow Cartridge 804: The micro-motor's gear-head was altered to accommodate an oscillating mechanism, which in conjunction with a custom-made dual channel flow cartridge, allows simultaneous pulsatile flows of both blood and the dialysate at controllable flow rates of 40-100 cc/min per channel. There was no connection between the two channels and the design of the dual channel pump cartridge 804 allowed the two liquids to flow either in the same direction or in opposite directions, depending on the need and the configuration/location of the other system components. The dual channel flow cartridge 804 comprises standard FDA approved PVC tubing, standard FDA approved Delrin occluders, standard FDA approved Latex holders, all housed in a Lucite housing that fits onto the micro-motor housing, as shown in FIG. 13.

The valves at either end of each channel 902, 904 in the flow cartridge 804 are one way valves that open when pressure in the positive fluid flow direction is applied to them. The intake valve 922 comprises an inlet 924, an o-ring 926, a manifold head inlet 928, an occlusion ball 929, a mercedies spring 930, and a peristaltic tubing adaptor 932. When the peristaltic tubing 934, attached to the peristaltic tubing adaptor 932, is expanding or decompressing after being pressed by a pushing mechanism 906, suction is created on the intake valve assembly 922 such that the ball 929 presses against and flexes the mercedies spring 930 thereby allowing the occlusion ball 929 to move away from the o-ring 926 and thereby allowing fluid to flow through the intake valve assembly 922 into the peristaltic tubing's flexible chamber 908.

Figure 16:
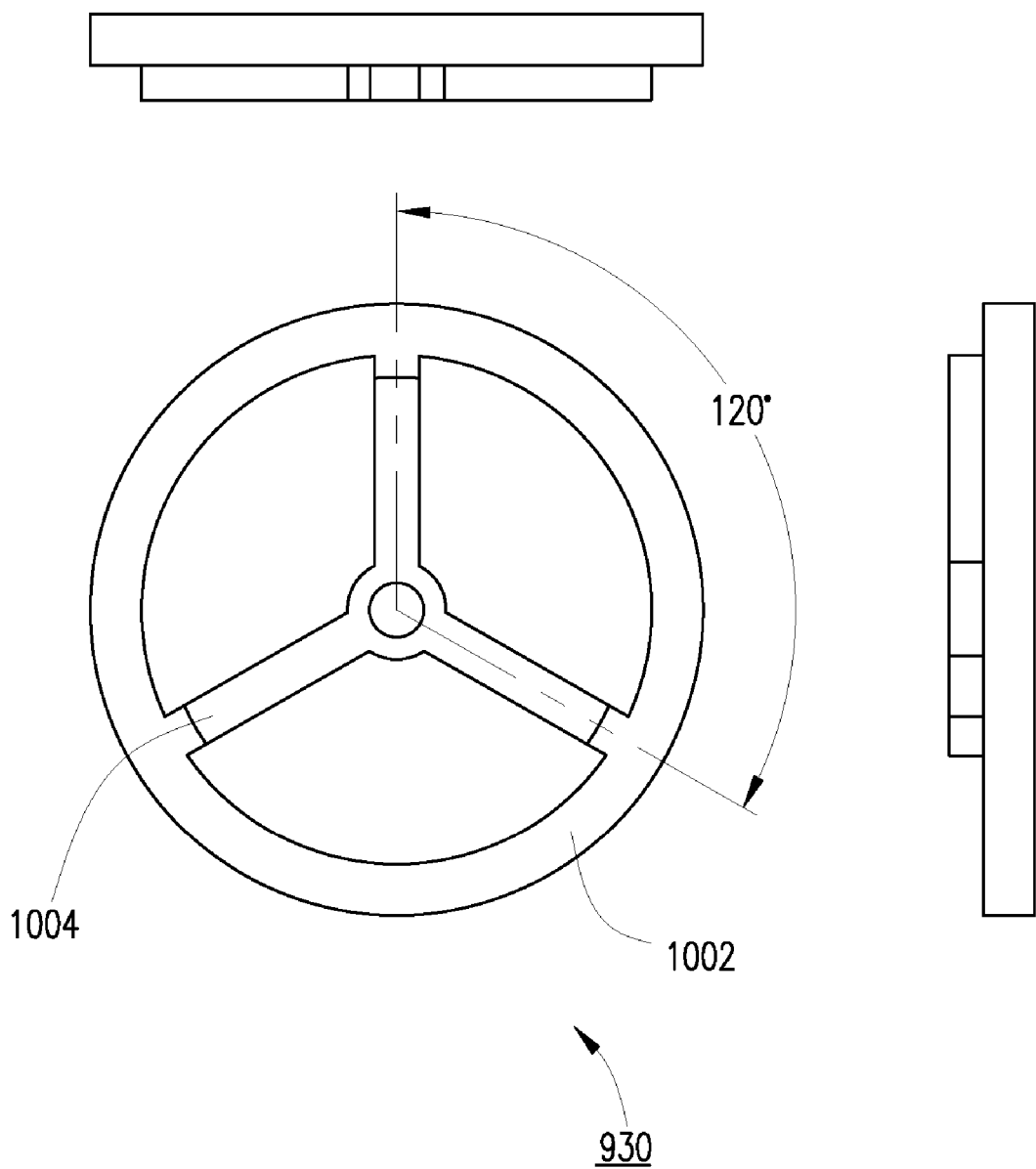
FIG. 16 is a three view of an exemplary spring used in an exemplary input or output valve.

Referring to FIG. 16, an exemplary front and side view of a mercedies spring along with various exemplary dimensions are shown. The mercedies spring 930 is made from a polymer, much like the o-ring 926, but could be made of a metal, a plastic, or a composite material. The mercedies spring 930 comprises two concentric rings; an inner ring 1000 and an outer ring 1002. Three spokes 1004, each extending radially from the inner ring 1000 to the outer ring 1002 connect and stabilize the positioning of the inner and out rings. The inner ring 1000 was found to act as a stabilizer and positioning place for the occlusion ball 929. It was further found that the inner ring 1000 helps to minimize rattling or oscillating movements of the occlusion ball 929 during fluid flow thereby providing a higher fluid flow rate than other exemplary occlusion valves. The inner ring 1000 of the mercedies spring also centers the ball so that the valve can close promptly as fluid flow decreases. The inner ring 1000 also operates to center the ball 929 on the o-ring 926 when the intake valve 922 is in a closed position and significantly limits the amount or stops all potential back-flow of fluid through the valve 922 when the peristaltic tubing 934 condition changes from a decompression state to a compression state and the pushing mechanism 906 is pushing against the peristaltic tubing 934. In another embodiment, the mercedies valve 930 may be replaced with a valve having an inner ring 1000, an outer ring 1002 and only two radial spokes 1004 that extend from the outer ring 1002 to the inner ring 1000. If two spokes 1004 are used, such spokes should be positioned substantially opposite or 180 degrees from each other. The inner ring 1000 and outer ring 1002 are shown to be concentric rings, but alternate embodiments of the invention may have non-concentric inner and outer rings.

The output valve 936 is connected to the peristaltic tubing 934 via another peristaltic tubing adaptor 932, an o-ring 926 acts as a sealing seat for the ball 929, which is inside the outlet manifold 938. A second mercedies spring 930 flexes when pushed by the ball 929 to allow fluid to flow through the output valve 936 when the peristaltic tubing 934 is being compressed by a pushing mechanism 906. Again, the dual concentric rings 1000, 1002 of the mercedies spring 930 stop chatter of the ball 929 during fluid flow thereby maximizing fluid flow and keeping the fluid flow smooth as it travels through the output valve 936. Chatter of the ball 929 is also undesirable because it can damage blood cells as blood flows through the exemplary valves of the pulsatile pump. Further, the mercedies valve 930 closes the valve and seats the ball 929 against the o-ring 926 smoothly when compression of the peristaltic tubing stops so that limited or no backflow occurs through the valve and so that there is limited damage to blood cells traveling through the blood channel of the dual channel pulsatile pump cartridge 800.

An exemplary dual channel pulsatile pump 800 comprising a pump-motor portion 802 and a dual channel pump cartridge 804 underwent an in-vitro reliability test for a week at the applicant's facility at Cedars-Sinai Medical Center in Los Angeles, Calif. De-ionized water having the same density and viscosity as dialysate was used in the dialysate channel. A mixture of approximately 40% glycerin in water at room temperature with a viscosity of 3.5 cp was used as a blood replacement liquid in the blood channel. Flow rate data was obtained and recorded by a clap-on ultrasonic flow probe (model 2XL) connected to a T110 ultrasonic flow meter (Transonic Systems, Ithaca, N.Y.) generating an output signal of ±1 Volt, which was imported to a LabView based data acquisition system, integrated in a stand-alone work-station.

The hemolysis properties of the model dual-ventricle pump cartridge were evaluated, following a protocol based on ASTM Standard F-1841-97. Running at a maximum operational blood flow of 78 ml/min and a pressure different of 100 mmHg, the average plasma free hemoglobin, adjusted for the relevant static control, was about 5 mg/dL/hr. These results suggested that an exemplary dual channel pulsatile pump will hemolyze within acceptable bounds when manufactured in its final and improved form, given the wide range of published data. To examine this point, the same hemolysis protocol was used on three commercial dialysis roller pumps as well. The corresponding plasma free hemoglobin was about 3 mg/dl/hr at 450 ml/min flow. Considering that a total of 5 dL (500 ml) flood was available to each pump for the six-hour tests, the hemoglobin destruction rates corresponding to exemplary dual channel pulsatile pump and the roller pumps were 25 and 15 mg/hr, respectively. Since a certain pump running at a certain flow rate would logically damage the same mg/hr rate hemoglobin no matter how much blood is available, this estimation might well apply to a patient with 5 liter of blood. If an average of 25 mg/hr could be practically acceptable (at a blood flow rate of about 78 ml/min,) then the patient would loose about 0.6 gm/day of hemoglobin. Note that an average erythrocyte weighs about 0.055 nano-gram and some 200 billion/day of it is produced in a healthy human, thus 11 gm/day. However, this would not happen in an ESRD patient without supplements such as Epogen, etc. A prospective dual channel pump user could loose about 1.7 gm/day erythrocyte, based on 0.6 gm/day hemoglobin loss and a hemoglobin/ erythrocyte ratio of 0.35. If ESRD patient's body could maintain at least 130 gm/lit erythrocyte, the mentioned assessed hemolysis would not create any problem, accounting for only 0.25% of the total 650 gm erythrocyte.

The results from the hemolysis tests mentioned above also showed a Normalized Index of Hemolysis (NIH) of about 0.4 mg/dL. The NIH, also called Hemolysis Index (HI) in literature, is a measure of the added grams of plasma free hemoglobin per 100 L of blood pumped, corrected for plasma volume using hematocrit and normalized flow rate and circulation time. The typically reported HI values are between 0.1 and 0.2 mg/dL, due to the fact that the standard dialysis roller pumps operate at flow rates several times higher than the exemplary dual channel pumps.

Regardless, it is understood that other types of pumps 724 (FIG. 12) other than pulsatile pumps can be successfully used or incorporated into embodiments of the wearable ultrafiltration device as long as power consumption is kept low enough for battery operation. The power consumption of the pump or pumps should be less than about 5 watts and it would be even better between 1 and 3 watts were required. Two separate single channel pumps may be used. Such other types of pumps include, but are not limited to, a shuttle pump, a piston pump, a roller pump, a centrifuge pump, a piezo electric pump, or other conventional pumps. Whatever pump is utilized, the pump(s) 724 should have a manually or electrically adjustable flow rate ranging between 20 ml/min and 120 ml/min and require between 1 and 5 watts.

Figure 17:
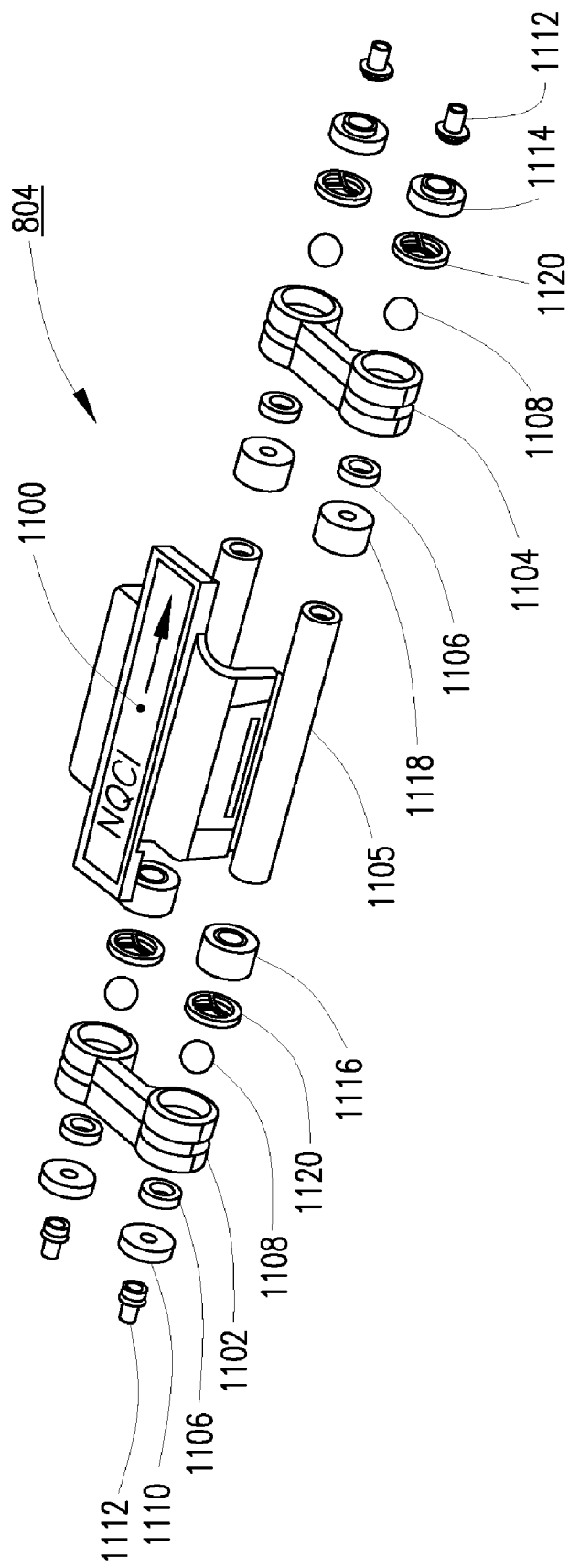
FIG. 17 is an exploded view of an exemplary dual channel pulsatile pump cartridge.
Figure 18A:
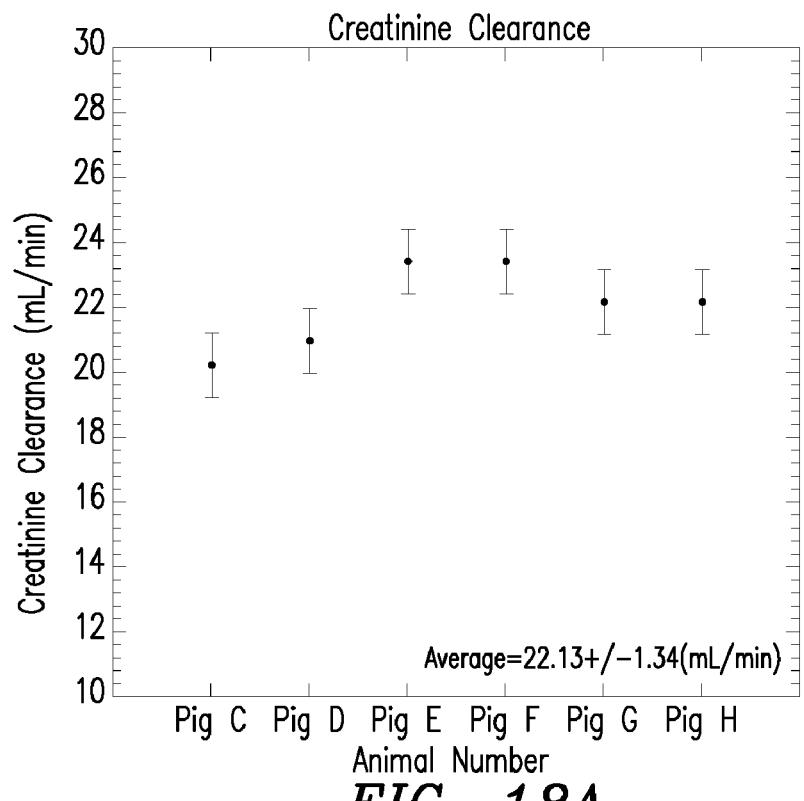
FIGS. 18A-18E are graphs indicating experimental results using an embodiment of the wearable CRRT device.
Figure 18B:
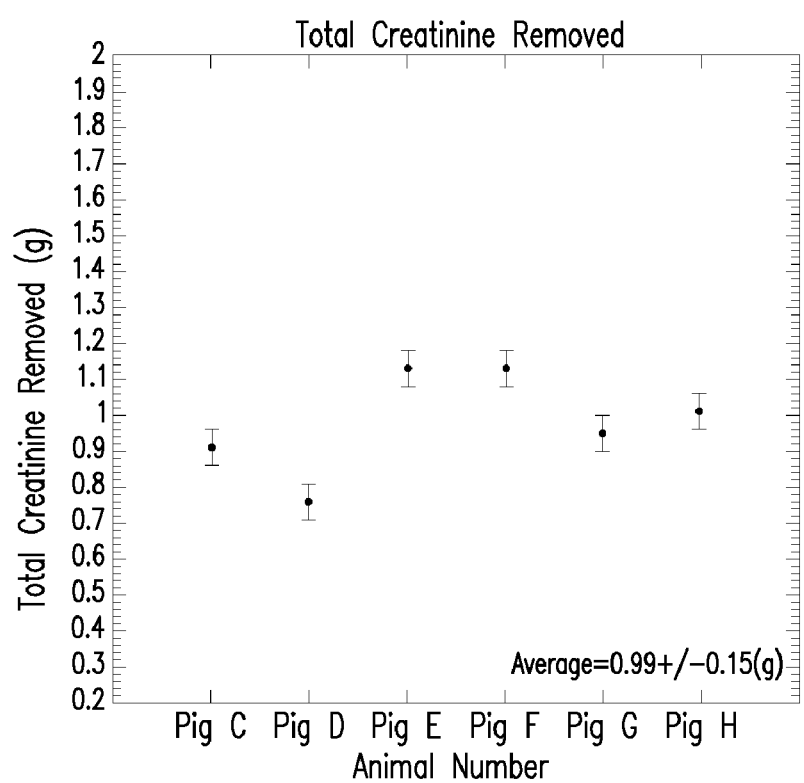
Figure 18C:
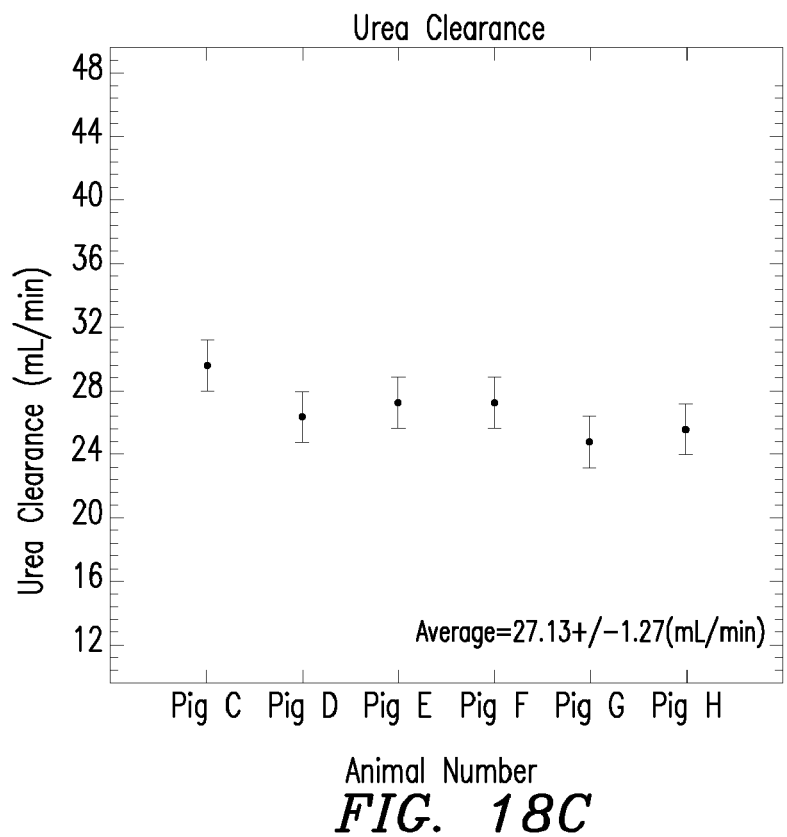
Figure 18D:
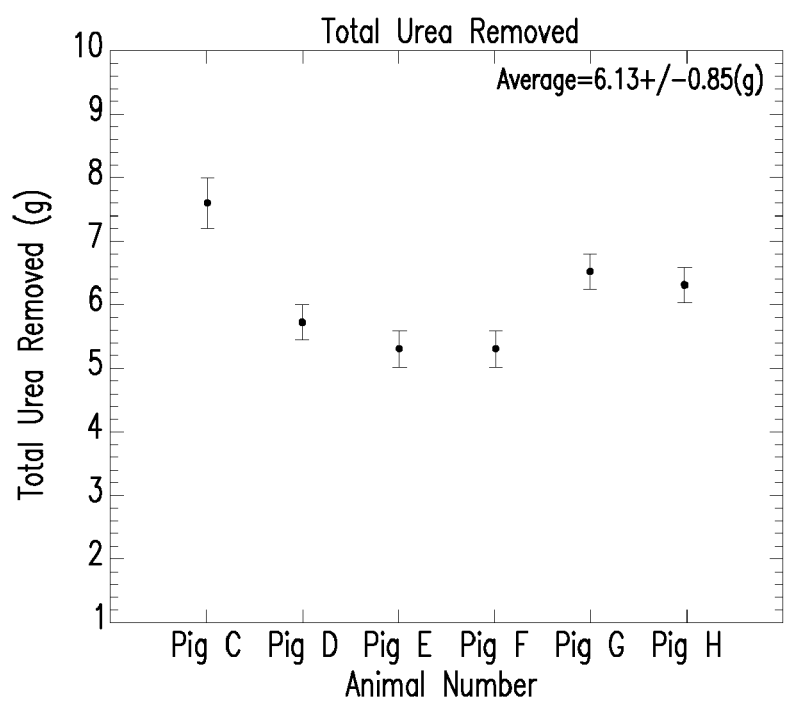
Figure 18E:
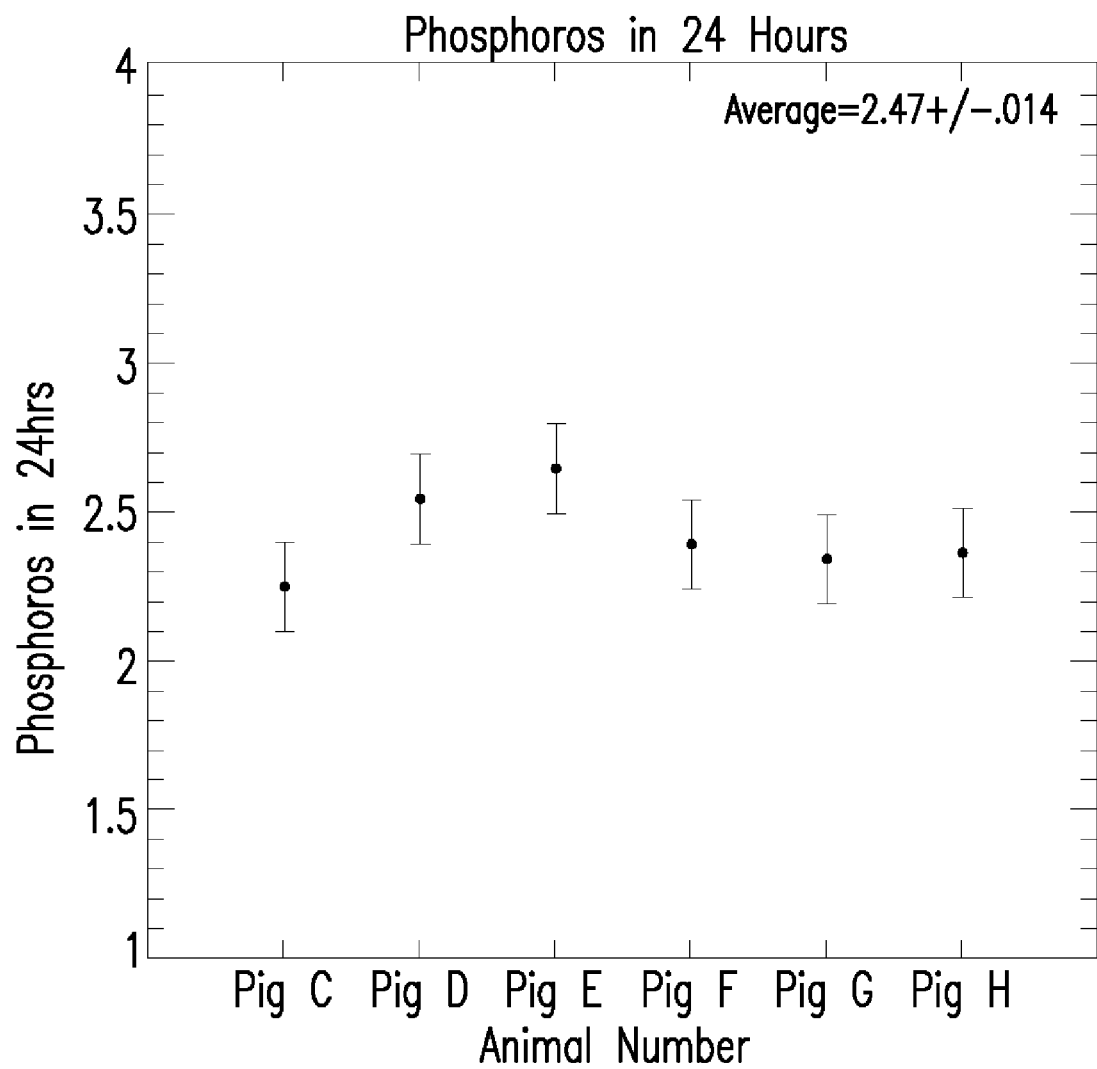

FIG. 17 provides and exploded view of an exemplary dual channel pulsatile pump cartridge 804 according to an embodiment of the invention. A center plate 1100 acts as a chassis for the dual fluid channels. Each fluid channel in this exemplary embodiment comprises an inlet manifold 1102 and outlet manifold 1104. Peristaltic tubing 1105 provides a squeezable or squashable flexible chamber that is resilient deformation by the pushing mechanisms of the mechanical pump elements. Tangential ball seats 1106 are used to seat the ball 1108 in a valve-closed position. An O-ring may be included along with or as a replacement to the tangential ball seat 1106. An occlusion ball 1108 is used to occlude or allow flow through each valve. The ball may be made of a plastic a polymer or a metal. At the inlet end a barb adapter 1110 and a bondable barb 1112 may be used aid in the connection of fluid tubing to the inlet side of a fluid channel. Similarly, on the outlet side an outlet barb adapter 1114 and a bondable barb 1112 may be used to connect fluid tubing to the output side of a channel. Peristaltic tubing adapters 1116, 1118 are used at the inlet side 1116 and the outlet side 1118 of the peristaltic tubing 1105. And, a mercedies spring 1120 is positioned such that the concentric inner ring moves perpendicular to the outer ring in the direction of fluid flow when a positive fluid pressure in the direction of fluid flow is placed on the ball 1108. When positive pressure is not present, the mercedies spring 1120 presses the ball 1108 against the tangential ball seat thereby sealing the path and stopping fluid flow in a reverse direction.

Referring back to FIG. 12, the microcontroller 714 may display pump status or other pump related information on the display 720. User controls 723, being buttons, switches, slide controls, knobs, connectors, or infrared receiver (not specifically shown) may be used to enable a patient, physical, nurse, technician or computer based device to adjust various settings and controls on an exemplary ultrafiltration device 700. Furthermore, the communication device 725 may be utilized to receive control settings and send information via paging or other telecom communication channels. For example, the adjustments to the pump 724 pump rate, torque, valve opening size, output pressure, flow rate, rpm, and on/off may all be monitored or controlled via the user interface 723 or the communication device 725.

Discussing the exemplary blood circuit 727 first, blood from the patient enters the blood circuit 727 via the blood inlet tube 726. An input blood pressure transducer 728 measures the input blood pressure and provides an input blood pressure signal to the microcontroller 714 (connection to microcontroller not specifically shown). The input blood pressure may be an average pressure of the blood prior to entering the pump 724*a*. The blood is then pumped through the pump 724*a*.

After the blood passes through the main pump 724*a*, it continues in the blood circuit 727 via the blood inlet tube 726. An input blood pressure transducer 728 measures the input blood pressure and provides an input blood pressure signal to the microcontroller 714 (connection to microcontroller not specifically shown). The input blood pressure may be an average pressure of the blood prior to entering the pump 724*a*. The blood is then pumped through the pump 724*a*.

After the blood passes through the main pump 724*a*, it continues in the blood circuit 727. A reservoir 734 containing a blood thinner or anticoagulant such as heparin or another acceptable anticoagulant additive is connected to the blood circuit via a micropump 736. The micropump 736 provides the fluid contents of the reservoir 734, in a measured continuous or non-continuous manner, to the blood circuit 727 prior to the dialyzer 730. (It is possible to connect the reservoir 734/pump 736 combination to the blood circuit before the pump 724*a*.) The micropump 736 is a type of pump that can pump microscopic or miniscule amounts of fluid each minute. A micropump, in general, may pump fluid at a rate ranging from 0.1 to 400 ml/hr (milliliters per hour). A micropump requires from about 1 to 500 milliwatts to operate. There are, at present, various pumps that can be considered micropumps including, but not limited to, a piezoelectric pump, a solenoid pump, a micro-piston pump, a peristaltic pump, a nanotechnology related pump, microtechnology/micromachined pump, syringe style pump, roller pump, centrifuge style pump, or diaphragm style pump.

The blood thinner and/or anticoagulant may be mixed or combined with the blood in the blood circuit at any point between the inlet of blood inlet tube 726 and the blood input side of the dialyzer 730.

The reservoir 734 may have a fluid level sensor 735 or other type of sensor to sense the amount of fluid available in the reservoir 734. The sensor 735 provides a signal to the microcontroller 714 indicating an amount of fluid in the reservoir 734. The microcontroller 714 sends an alarm signal to the alarm circuit 718 if the fluid level or fluid amount in the reservoir 734 is below a first predetermined amount or volume. The microcontroller 714 may also turn the ultrafiltration device 700 off if the fluid level in reservoir 734 is at the first predetermined level or below the first predetermined level and at a second predetermined level.

The combination of the reservoir 734 and the micropump 736 infuse the blood thinner or anticoagulant into the blood flowing in the blood circuit 727. Again, the thinner or anticoagulant is infused into the blood prior to the dialyzer (or blood filter) 730 (in some embodiments prior to the blood pump 724*a*) in order to help minimize the potential of blood clots in the blood filter 730 and perhaps in the blood pump 724*a*.

A second pressure transducer 733 senses the pressure in the blood circuit after the blood pump 724*a*, but before the dialyzer 730. The pressure reading is supplied to the microcontroller (MC) 714 which monitors such readings.

A dialyzer 730, shown as a single dialyzer, can be a single or multiple dialyzer as discussed earlier. The dialyzer(s) may take the form of a cartridge that can be "clicked" or inserted into and out of the blood/dialysate circuits by a doctor, nurse or technician. The dialyzer may comprise from 0.2 to 1 sq. meters of dialyzing surface area. During dialysis the blood circuit 727 flows in the opposite direction as the dialysate circuit 729 in order to help maximize the dialysis process. Furthermore, the pulsing of the pumps 724*a* and *b* may, either in phase or out of phase, also aid in maximizing the dialysis processes.

The blood, after being dialyzed in the dialyzer 730, exits the dialyzer 730 and flows through a third pressure transducer 737. The third pressure transducer 737 provides a pressure signal to the microcontroller. The combination of the first, second and third transducers provide differential pressure measurements that are analyzed by the microcontroller 714. For example, if the pressure differential across the dialyzer 730 is too high it may mean, among other things, that the dialyzer 730 has a clot in it or is being operated at too high a blood flow. As a result, an alarm situation can be initiated or the blood pump 724*a* pumping rate or torque can be adjusted via microprocessor control. If the pressure at a transducer drops below a predetermined pressure it may be an indication of a fluid leak or that air is in the blood circuit 727. The microcontroller 714 may shut down all or predetermine parts of the wearable CRRT device 700 in response to pressure measured below a predetermined level.

The blood returns to the patient via the blood outlet tube 740. As shown in FIG. 4, a sideport 200 can be incorporated so that additional electrolytes, drugs, blood additives, vitamins or other fluids can be added to the blood in the blood circuit 727 via a reservoir/micropump combination prior to the blood being returned to the patient via the blood outlet tube 740.

Referring still to FIG. 12, the exemplary dialysate circuit will now be discussed. A fourth pressure transducer 750 measures the dialysate pressure at the input side of the dialysate pump 724*b* and provides the pressure reading to the microcontroller 714. The dialysate pump 724*b*, like the blood pump 724*a* is preferably part of a dual pump device 724 described above, but may be a separate pump device.

Cleaned, fresh dialysate from the sorbent filters 769 flows in the dialysate circuit 729 through the dialysate pump 724*b*. The dialysate pump 724*b* can pump dialysate at a flow rate ranging from near zero to 150 ml/min. The exemplary normal operating flow rate of the dialysate pump is between 40 and 100 ml/min.

Embodiments of the wearable CRRT device 700 are designed to operate using less than one liter of dialysate. Embodiments preferably only require 300 ml to 400 ml in the closed dialysate fluid circuit 729 to operate. An embodiment designed for a young adult or child may operate with about 100 to about 300 ml of dialysate. The combination of dialysate and filters 769 allow an embodiment to circulate dialysate for at least 24 hours before a filter requires replacement. Furthermore, because less than a liter of dialysate is all that is needed in the closed dialysate circuit 729, sterile or ultra-pure dialysate can be economically used in exemplary embodiments of the WAK or wearable CRRT device 700.

In normal or large dialysis machines it is common to use about 90 liters of dialysate per patient per run. Generally, due to of the amount of water required to create the dialysate, filtered water, rather than ultra-pure water, is used. Filtered water is much less expensive than ultra-pure or sterile water. Filtered water that is used in dialysis machines is allowed to have some bacteria in it. The bacteria are larger than the size of the pores in the membranes used in the dialyzer 730. Since the bacteria is larger than the pore size, the bacteria cannot cross the membrane and get into the blood.

Conversely, medical research has provided some results that are uncomfortable with the use of non-sterile dialysate (dialysate containing filtered water, bacteria, toxins, or micro organisms). The micro organisms and bacteria create waste products, toxins or poisons in the dialysate. The waste products from the bacteria can cross the dialyzer pores and get into the patient's blood while the actual bacteria cannot. Such toxins are referred to, in some cases, as endotoxins. The endotoxins that pass from the dialysate to the blood can have a negative effect on the patient's health. The endotoxins can make the patient sick.

Since exemplary embodiments of the wearable CRRT device 700 require less than one liter of dialysate it is economically feasible to use ultra-pure or sterile water when making the dialysate.

The dialysate exits the dialysate pump 724b, passes by another pressure transducer 752, which measures the dialysate pressure on the input side of dialyzer 730. The dialysate circuit 729 moves the dialysate into the dialyzer 730 such that the dialysate preferably moves in a direction opposite to the flow of blood through the dialyzer. While the dialysate is in the dialyzer to the dialysate 730, waste products and toxins in the blood pass through the membranes of the dialyzer to the dialysate thereby cleaning the patient's blood.

The dialysate exits the dialyzer 730 and flows through another pressure transducer 754. The pressure transducer 754 on the output side of the dialyzer 730 sends a signal to the microcontroller 714 indicating the pressure of the dialysate. The pressure may help indicate a clogged dialyzer, a leak or other emergency condition.

The dialysate circuit 729 takes the used, toxin or contaminant containing, dialysate to the first of a series of dialysate filters 769. The filters may filter or react with predetermined substances in the dialysate in order to recycle the dialysate for continued use in the dialysate circuit.

In an exemplary embodiment, the first filter 760 contains urease. The urease filters the used dialysate and further functions to break down urea that was removed from the blood in the dialyzer 730. When urease breaks down urea at least two unwanted bi-products are created. Generally, the two bi-products are ammonium (ammonia) and carbon dioxide.

The dialysate with the ammonia and carbon dioxide exit the first filter 760. The urea is substantially removed from the dialysate, but the ammonia and carbon dioxide need to be removed from the dialysate also. The dialysate, ammonia, and carbon dioxide enter the second filter 762. The second filter 762 contains a compound containing zirconium or zirconium phosphate (i.e., ZrPx). The zirconium in the second filter 762 captures the ammonia. It is understood by those having ordinary skill in the art of dialysis chemistry that various chemicals and derivations thereof can be utilized to achieve the same or similar results.

The zirconium filter, the second filter 762, will eventually become saturated with ammonia. The zirconium filter, when becoming saturated with ammonia, will become less efficient at removing ammonia from the dialysate. It is not advantageous to allow ammonia or ammonium to circulate through the dialysate circuit 729. Thus, in an exemplary wearable CRRT 700, a sensor 764 is placed in the dialysate circuit 729 to sense a presence of ammonia in the dialysate. The sensor 764 may be a ph sensor, an ammonia specific sensor, or a conductivity sensor. If an ammonia sensor is used it will sense whether a predetermined amount of ammonia is present in the dialysate. If a ph sensor is used, it would sense whether the ph of the dialysate has become a predetermined amount more alkaline than normal. When ammonia is present, the dialysate becomes more alkaline. It is noted that depending on the actual chemicals and absorbents used in the filters, the dialysate may become more acidic and as such a sensor would be used to sense the same. If a conductivity sensor is used, it will sense the conductivity changes of the dialysate.

The sensor 764 is in electrical communication with the microcontroller 714. If the signal read by or provided to the microcontroller 714 from the sensor 764 indicates that the second filter 762, the zirconium filter, is not adsorbing a majority or a predetermined amount of the ammonia in the dialysate, then an alarm condition is triggered by the microcontroller 714. The alarm condition would instruct the user that one or more filters (cartridges) need to be replaced. The alarm condition may also shut down predetermined functions of the wearable CRRT device 700. For example, one or more pumps 724 may be shut down or the pump rate of one or more pumps and micro pumps may be slowed. Slowing the pump rate may increase the amount of ammonia adsorbed by the zirconium based filters in the sorbent filter section 769.

The sensor 764 that is used to sense the presence of ammonia in the dialysate is placed after the second filter 762 containing the zirconium phosphate. The sensor 764 may be placed after the third filter 766, that contains hydrous zirconium oxide or the fourth filter 768 which is a carbon filter. One or more sensors in the dialysate circuit will sense pressure, pH, ammonia, flow rate, temperature or other physical attributes. A sensor will provide a signal to the microcontroller indicating that the dialysate circuit needs maintenance.

The third exemplary filter 766 is a hydrous zirconium oxide (ZrOx) filter which may further remove contaminants and ammonia from the dialysate. A bubbler degasser, or valve device 770 may be part of a filter (i.e., 762, 766 or 768) or be a separate element, as shown, removes air, carbon dioxide and other gas bubbles from the dialysate. It is important that a limited amount of gas bubbles go through the dialyzer 730. As such a bubbler 770 (one or more) should be positioned prior to the pump 724b, but after the filter or filters that may cause gas bubbles to form in the dialysate.

The fourth exemplary filter 768 contains carbon and is used to further clean the dialysate of impurities via adsorption. The filters, as discussed previously, are preferably designed as filter cartridges. Each cartridge can be inserted and removed from the wearable CRRT device 700 by the patient, doctor, technician or nurse. Each filter cartridge 760, 762, 766, 768 may contain layers or combinations of chemicals or adsorbents. In fact, an exemplary embodiment may have a single cartridge filter containing layers of required substances to clean and refresh the dialysate after passing through the dialyzer 730. The filter cartridge(s) may each incorporate a bubbler device or the bubbler 770 may be a separate element in the dialysate circuit 729.

In an exemplary wearable CRRT device 700 the cartridge(s) may be replaced daily or every other day by the patient. Each filter cartridge should weigh less than half a pound dry. The combination of all the cartridges, dry, should weigh less than two pounds total. Each filter cartridge may have inner dimensions of about 4 cm×10 cm×10 cm or provide a volume of about 400 $cm^3 \pm 100$ $cm^3$ for each sorbent material. The total volume of all sorbent materials using in whatever quantity, combined, may be between about 400 $cm^3 \pm 2,000$ $cm^3$. In an exemplary embodiment a filter cartridge can be changed one a day or less often.

An additive reservoir 772 and micropump 774 may be connected to the dialysate circuit 729 after the filter cartridge(s) 769, but before the pump 724b. Although not specifically shown in FIG. 12 multiple reservoirs 772 and micropumps 774 can be connected to the dialysate circuit 729. The micropump(s) 774 may be any of the micropumps discussed above with respect to micropump 736. Here the micropump(s) 774 and reservoirs 772 may add chemicals and additives to freshen the dialysate and prolong its ability to act as a dialysate. An exemplary wearable CRRT device 700 may have as little as 300 ml to about one liter of dialysate in the dialysate circuit 729. It is important for the sorbent section 769 to be able to clean and freshen the dialysate continuously as it circulates about the dialysate circuit 729.

An exemplary wearable CRRT device 700 may also remove ultrafiltrate or fluids from the patient's blood. The patient's kidneys may not be functioning properly. After the dialysate leaves the dialyzer 730, and preferably before the dialysate enters the filter cartridge(s) 769, ultrafiltrate/dialysate, along with other contaminants and fluids obtained via the dialyzer 730, can be removed from the dialysate circuit 729 via a valve 776 and deposited in a fluid bladder 778. The fluid bladder 778 may hang below the wearable CRRT device 700 (not specifically shown) and be able to store from about 0.1 to 2 liters of fluid. A fullness sensor associated with the fluid bladder 778 is in electrical communication with the microcontroller 714 to enable an alarm condition when the fluid bladder 778 at a predetermined fullness.

The fluid bladder 778 may also be incorporated into the wearable CRRT device 700 as an empty cartridge that is filled via a micropump and valve combination 776. A fullness sensor 780 can aid the microcontroller to determine the fullness of the cartridge bladder 776 will turn off the ultrafiltrate supplying micropump 776 and provide a signal to the user that the cartridge needs emptying. The fluid bladder or cartridge 778 may contain an absorbent material (not specifically shown) for absorbing fluid presented to the bladder 778. The absorbent material may be a cotton, polymer, sponge, compressed material, powder, jell or other material that absorbs fluid and/or limits sloshing in the bladder or cartridge. The bladder may be designed to expand as it fills. The bladder may press against a microswitch 780 (not specifically shown) when it is full thereby providing a signal to the microprocessor 714.

The fluid bladder or cartridge 778 may have a means for emptying the fluid bladder 782 thereon in the form of a cap, stopper, valve, removable inner bladder or otherwise.

Referring back to the blood circuit in FIG. 12, reservoir/micropump combinations 784 (piezo pumps, solenoid pumps, syringe pumps, etc.) can be connected to the output side of the blood circuit dialyzer 730, 727. One or more micropumps and fluid reservoirs 784 can be connected. Additional heparin, electrolytes, blood additives, drugs, vitamins or hormones can be added to the dialyzed blood returning to the patient's body. The reservoir/micropump combinations are monitored and controlled by the microcontroller and can be adjusted via the user controls 723, or instructions received via the communication device 725.

Exemplary embodiments of the wearable CRT device can provide therapy from a basic dialysis function to a more complex medical dialysis, ultrafiltration, and medicinal therapy to a patient.

As discussed, there continues to be a growing body of literature indicating that increasing dialysis time, being longer or more frequent dialysis treatments, may be associated with improved outcomes in the treatment of End Stage Renal Disease (ESRD) patients, both in terms of life quality as well as expected morbidity and mortality.

However, the implementation of such modalities of treatment is complicated because of the lack of readily available economic resources to pay for the increased time or more frequent dialysis treatments. Furthermore, even if the money to pay for more dialysis time or treatments was available, there is currently limited additional nursing or technician manpower to deliver much more additional care. In addition, construction of additional facilities would be necessary to accommodate all these additional needs. Given the budgetary constrains of health care budgets in most countries, the chances of any or all of these things occurring is slim. Furthermore, very few dialysis patients are suitable for home self-treatment on non-wearable dialysis devices.

Embodiments of the wearable CRRT device are generally worn on a belt or strap by the patient and can be used for continuous renal replacement therapy twenty-four hours a day, seven days a week. Such embodiments can deliver significantly higher doses of dialysis than the intermittent dosing commonly administered by dialysis facilities today, while at the same time achieving significant reductions in manpower utilization and other medical related costs.

Recently an embodiment of the invention was tested to assess the efficiency and viability of the inventions in a uremic pig model. The efficiency of the exemplary wearable CRRT device was evaluated by achieving the removal of urea, creatinine, potassium, phosphorus and ultrafiltrate in amounts that would normalize the volume status as well as the above chemistries in uremic humans if the device would be worn continuously. Furthermore, the efficiency of the device was tested by achieving dialysis doses that would be equal to or higher than those afforded by intermittent daily dialysis, as measured by creatinine clearance, urea clearance and weekly urea Kt/V.

The exemplary embodiment of the wearable CRRT device used in the test comprised a blood circuit and a dialysate circuit. The blood circuit and dialysate circuit flowed through a small dialyzer that utilized polysulfone hollow fibers. The dialyzing surface area of the dialyzer was about 0.2 meters. The blood circuit had a port for the continuous administration of heparin into the circuit prior to the dialyzer. Both the blood and dialysate were propelled through their requisite circuits via a double channel pulsatile pump powered by replaceable batteries. The dirty or spent dialysate that exited the dialyzer was circulated through a series of filter cartridges containing urease and sorbents similar to those described by Marantz and coworker and widely used in the well known REDY system.

Ultrafiltrate was removed by the dialysate circuit via a valving structure. The removed ultrafiltrate was directed to and stored in a plastic bag that was periodically emptied after volume measurement. Sensors connected to a micropressure monitored various aspects of the exemplary device.

Six farm raised pigs each weighing approximately 150 lbs. were anesthetized and made uremic by surgical ligation of both ureters. Twenty-four to forty-eight hours later the animals were again anesthetized and a double lumen Mahurkar catheter was inserted in a jugular vein. The catheter was connected to the exemplary CRRT device and each animal was dialyzed for eight hours. At the end of the eight hours the animals were euphemized.

Blood samples were drawn from an arterial line inserted in the carotid artery and CBC, urea, creatinine, sodium, potassium, chloride, $CO_2$, phosphorus, calcium and magnesium were measured. The same chemistries were measured in the dialysate circuit at the input side of the dialyzer and at the exit side of each filter cartridge.

The results of the test experiment were as follows. There were no adverse events observed in the animals during the test experiments. The average blood flow rate in the blood circuit was 44 ml/min and the average dialysate flow rate was 73 ml/min. The results of the test experiments are summarized in Tables I and II.

TABLE 1

Amount of Fluid Removed (in ml.) from each Animal in Eight Hours

|  | Pig C (g) | Pig D (g) | Pig E (g) | Pig F (g) | Pig G (g) | Pig H (g) |
|---|---|---|---|---|---|---|
| 1 hr. | 400 | 100 | 100 | 100 | 150 | 180 |
| 2 hrs | 700 | 200 | 200 | 200 | 220 | 200 |
| 3 hrs |  | 300 | 200 | 300 | 380 | 350 |
| 4 hrs | 800 | 400 | 250 | 400 | 500 | 700 |
| 5 hrs |  | 500 | 300 | 500 | 600 | 710 |
| 6 hrs |  | 500 | 500 | 800 | 690 | 1410 |
| 7 hrs |  | 620 | 600 | 1000 | 700 | 1400 |
| 8 hrs |  | 800 | 1000 | 1150 | 800 | 1400 |
| Average | 100 | 100 | 124 | 144 | 100 | 175 |

The amounts of potassium and phosphorous removed are expressed per twenty-four hours of treatment. The daily removal of potassium was 260.67±27.05 mmol/24 hrs. The daily removal of phosphorus was 2.47±0.14 gr/24 hours. The average creatinine clearance obtained with this exemplary embodiment was 22.13±1.34 ml/min. The average urea clearance was 27.13±1.27 ml/min and the weekly urea Kt/V was 5.97±0.44.

The lack of complications in the test experiments implies that the exemplary wearable CRRT device may be operated with the potential of no complications. The exemplary experimental wearable CRRT device has not displayed any complications differing from complications associated with existing large scale dialysis machines presently in use in the industry. The relatively low flow rates of the blood circuit and dialysate circuit help mitigate various complications found in some dialysis systems. Modifications can be made to the experimental exemplary CRRT device to allow an increase in the blood flow to range from about 50 to 120 ml/min. The modifications include at least one of increasing the size of the dialyzer, increasing the flow of the dual pump, and adjusting the transmission, gearing and valving of the pump.

The capacity of an exemplary wearable CRRT device to remove fluid steadily from the vascular space in amounts similar to the volume of fluids removed physiologically by normal kidney gives a treating physician the ability to keep a patient euvolemic, regardless of the amount of fluid the patient ingests. Further, the elimination of excess fluid may also result in better control of a patient's hypertension. The sodium concentration in the extracted ultrafiltrate is roughly equal to the sodium concentration of the patient's plasma. Thus, removal of about 0.5 to 3 liters of ultrafiltrate, via an exemplary CRRT device, a day will result in removal of about 10 to 20 grams of salt per day. Removal of sodium from a patient via an embodiment of the invention may contribute to better control of a patient's hypertension, and also result in liberalizing salt intake for ESRD patients. Thereby, perhaps improving a patient's quality of life by increasing the variety of foods a patient can eat. Furthermore, eating a variety of foods may result in improved nutrition for the patient.

TABLE II

Experimental Data Acquired from Six Pigs, Using the Exemplary CRRT Device

|  | Creatinine Clearance (mL/min) | Total Creatinine Removed (g) (8 hrs) | Urea Clearance (mL/min) | Total Urea Removed (g) (8 hrs) | Weekly std (Kt/V) Urea | Phosphorus (grams) (24 hrs) | Potassium (mmole) (24 hrs) |
|---|---|---|---|---|---|---|---|
| Pig C | 20.10 | 0.91 | 29.40 | 7.61 | 6.50 | 2.30 | 266.11 |
| Pig D | 21.10 | 0.76 | 26.80 | 5.75 | 6.20 | 2.60 | 259.91 |
| Pig E | 23.50 | 1.14 | 27.30 | 5.37 | 6.10 | 2.67 | 303.54 |
| Pig F | 23.50 | 1.14 | 27.30 | 5.37 | 6.00 | 2.44 | 270.50 |
| Pig G | 22.30 | 0.95 | 25.70 | 6.46 | 5.20 | 2.41 | 236.97 |
| Pig H | 22.30 | 1.02 | 26.30 | 6.24 | 5.80 | 2.42 | 227.01 |
| Mean | 22.13 ± 1.34 | 0.99 ± 0.15 | 27.13 ± 1.27 | 6.13 ± 0.85 | 5.97 ± 0.44 | 2.47 ± 0.14 | 260.67 ± 27.05 |

The fluid volume removed was changed arbitrarily during the experiment from 0 to about 700 ml/hr. The limiting factor for the removal of larger amounts of fluid per hour was a progressive decrease in blood flow in the dialyzer as the rate of fluid removal was increased. The blood flow normalized immediately as the rate of ultrafiltration (fluid removal) was decreased. There were no difficulties however in maintaining a fluid removal of 100 ml/hr. The amounts of urea, creatinine, and phosphorus are further shown in FIGS. 18A through 18E.

Also, the amounts of potassium and phosphorus removed from a patient's blood by an exemplary wearable CRRT device further helps eliminate restrictions on oral intake of both the elements, and the elimination of a need for oral phosphate binders.

The experimental results indicate that the amount of creatinine and urea removed, as well as the high dialysis dose, expressed in both clearances and weekly urea Kt/V would make it feasible to achieve all the benefits of presently provided intermittent daily dialysis doses. The experiment, at the same time, proved a potential for decreasing the use of medical manpower and other costs associated with chronic dialysis.

Figure 19:
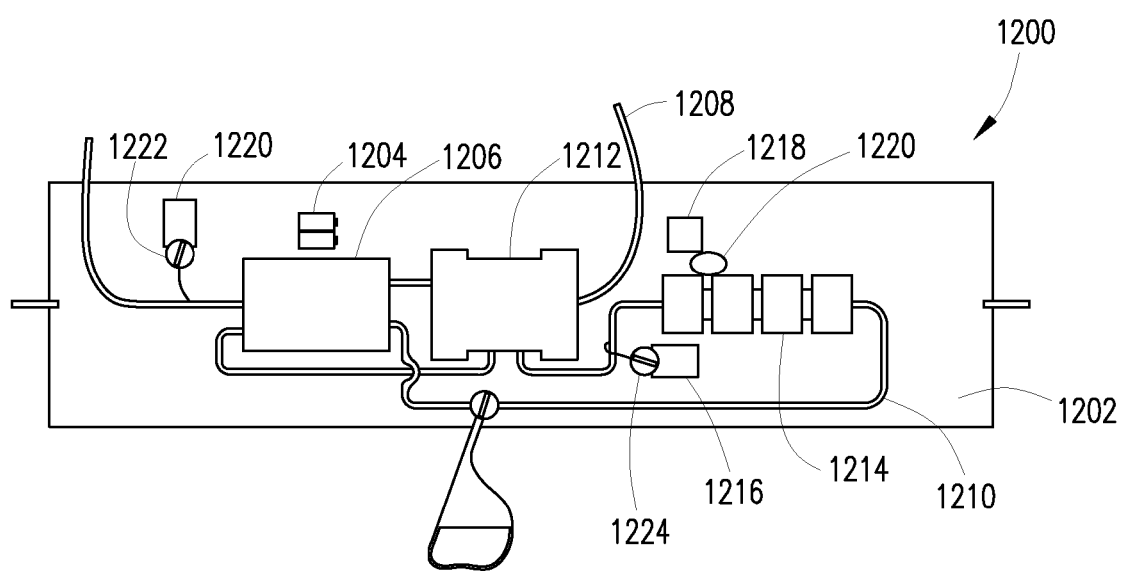
FIG. 19 is another exemplary embodiment of a wearable artificial kidney.

Referring now to FIG. 19, another exemplary WAK 1200 is shown as being incorporated into a completely wearable belt 1202. The WAK 1200 is a light-weight (between 0.5 and 5 pounds), belt-type, battery-operated 1204, WAK device 1200, which is comprised of the following main parts:

A. A dual channel pulsatile pump 1206 propels both blood 1208 and dialysate 1210 through the WAK 1200;

B. A high flux, AN-69 Dialyzer 1212 with 0.6 square meter membrane surface (Hospal Industrie, France);

C. A dialysate regeneration system 1214 comprising 1 to 5 specially designed cartridges and/or filters containing sorbents, as well as reservoirs 1216 of electrolyte additives and heparin 1220, and a pH-control circuit 1218;

E. Auxiliary micro-pumps 1222, 1224 for delivering heparin, Mg, Ca, K and Na Bicarbonate, and removing excess ultrafiltrate, all at pre-specified flow rates; and F. Microprocessor based control and monitoring (not specifically shown).

The dual channel pulsatile pump 1206 uses a 3-Watt DC micro motor (FAULHABER, Germany). The dual channel pulsatile pump 1206 has an oscillating mechanism and a dual channel flow cartridge allowing simultaneous pulsatile flows of both blood and dialysate at controllable rates of 40-100 ml/min. When one channel is propelling fluid out of its compressible chamber (as in "systole"), the other chamber is filling its compressible chamber (as in "diastole"), creating a peak pressure in one channel while the pressure in the other channel is at its trough or low.

The exemplary WAK of FIG. 19 uses a compact higher-membrane-surface (0.60-square-meter), high-flux AN69 Multiflow™ 60 dialyzer instead of a previously experimented with Hemophan® 0.22 square-meter dialyzer. A pH meter electrode 1220 was placed in the dialysate circuit and connected to the pH control system 1218. The pH control system 1218 was set to trigger a Na Bicarbonate infusion to the dialysate 1210 prior to the dialysates entrance into the dialyzer in order to maintain the pH of the dialysate at approximately 7.4. The urea and creatinine clearances and standard weekly urea Kt/V for the this exemplary embodiment were calculated as follows;

$$\text{Clearance} = \text{Blood Flow} \times [\Delta \text{ Solute}]/[\text{Solute in}] \quad (1);$$

$$\text{Standard Weekly } Kt/V = \text{Effective Clearance} \times \text{Time} / \text{Total Body Water} \quad (2);$$

Where [Δ Solute] is the difference between concentrations in and out of the dialyzer. "Time" was 480 minutes in the actual tests and 10,080 minutes for a weekly extrapolation. "Total Body Water" was estimated as 60% of body weight. Note that this calculation uses a uniform Effective Clearance averaged over the entire time period of one week.

Pump/Dialyzer Characteristics

To test the exemplary WAK 1200 using different pumping devices, the following pumps were used: the exemplary WAK's double-channel pump (10×7×5 cm, 380 gm) 1206, a Minipump™ (30×15×15 cm, 4650 gm. MINNTECH., MN) similar to the roller pumps used in HD, a MasterFlex® (30× 18×12 cm, 2950 gm. Cole-Parmer, IL) similar to the CRRT blood roller pumps, and a Profile™ (8×7×7 cm, 65 gm. Meikopet Corp., Japan) centrifugal pump.

Figure 20:
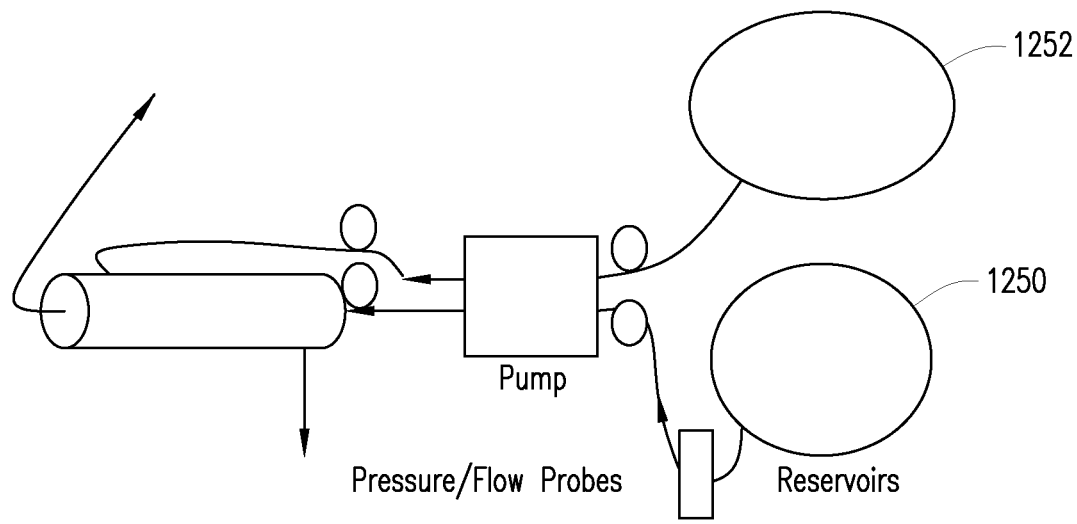
FIG. 20 is an exemplary test set up schematic for assessment of pump and dialyzer characteristics.

First, heparinized porcine blood 1250 was dialyzed with isotonic saline as dialysate 1252, (FIG. 20) using the aforementioned pumps and various dialyzers: Hemophan® (Model 100 HG, Gambro, Germany), AN69 (Multiflow 60, Hospal France), and F3® (Fresenius, Germany). Urea, Creatinine, and Potassium were added to the blood in order to elevate BUN to 60 mg/dL, Creatinine to 10 mg/dL, and K to 6 mmol/L. These additions were based on calculating the weights of whole-blood and respective chemicals, and recording the actual compositions using an i-STAT® Portable Clinical Analyzer (i-STAT Corporation, NJ.). Both fluids flowed in open-ended circuits at 37° C. The various pumps were run at several speeds. The Frequency of oscillation, speed, flows and pressures provided by the pumps in the circuit were recorded after stabilization of flow at every speed. Blood and dialysate samples were analyzed in duplicate using an i-STAT® Portable Clinical Analyzer (i-STAT Corporation, NJ) and a 990 Hitachi® Autoanalyzer. Gravity was used for continuous, non-pulsating flow of blood and dialysate. All experiments were repeated five times.

Sorbent Characteristics

Figure 21:
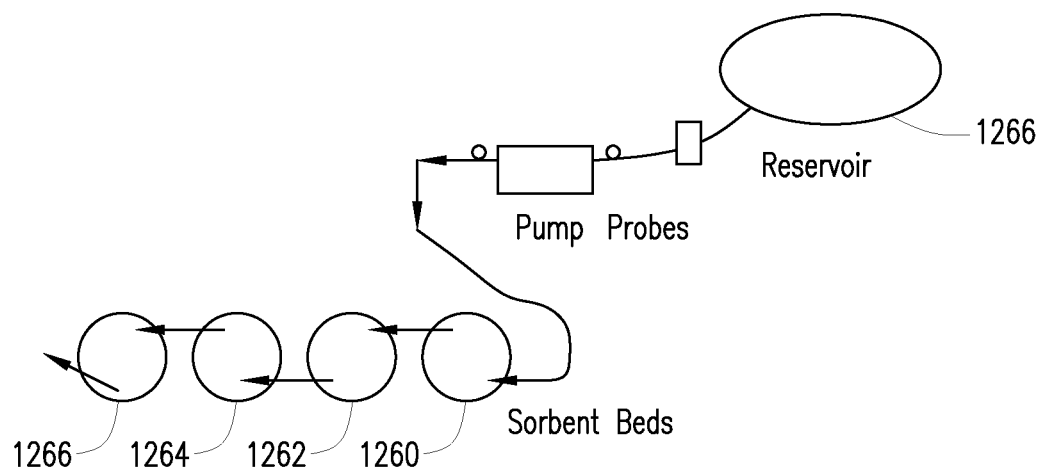
FIG. 21 is an exemplary test setup schematic for assessment of sorbent characteristics.

Next, the characteristics of the exemplary WAK's dialysate regenerating system 1214 were examined as shown in FIG. 21. The sorbents used included immobilized urease 1260, zirconium-phosphate 1262, hydrous-zirconium-oxide 1264 and activated carbon 1266.

Human spent dialysate 1266 was run through the system without modifications as well as with added Urea, Creatinine, Potassium, and Calcium to achieve levels of BUN 50 mg/dL, Creatinine 4 mg/dL, K 4 mEq/L, and Ca 9 mg/dL. As dialysate was circulated through the system, about 100 ml/hr of fluid were ultra filtered out. The dialysate was monitored for free Ammonia. The solute clearances from the dialysate vs. pump speed and flow rate were compared. All experiments were repeated 5 times.

Next, a 3 gm/L Urea/water solution was circulated through a combination of immobilized urease and a zirconium-phosphate using continuous, roller pump and pulsatile flows (WAK pump). The effluent was monitored for pH and ammonia. All experiments were repeated 5 times.

In-vivo Studies

Additional studies and testing were performed in-vivo using an exemplary WAK 1200. All animal studies were approved by the Institutional Animal Care and Use Committee of Cedars Sinai Hospital and according to NIH guidelines for animal experimentation. Five anesthetized pigs underwent surgical ligation of the ureters. The next day they were dialyzed for 8 hours using a double lumen catheter, with an exemplary WAK 1200.

RESULTS

Flow/Pressure Waves Generated by Pumps

Figure 22:
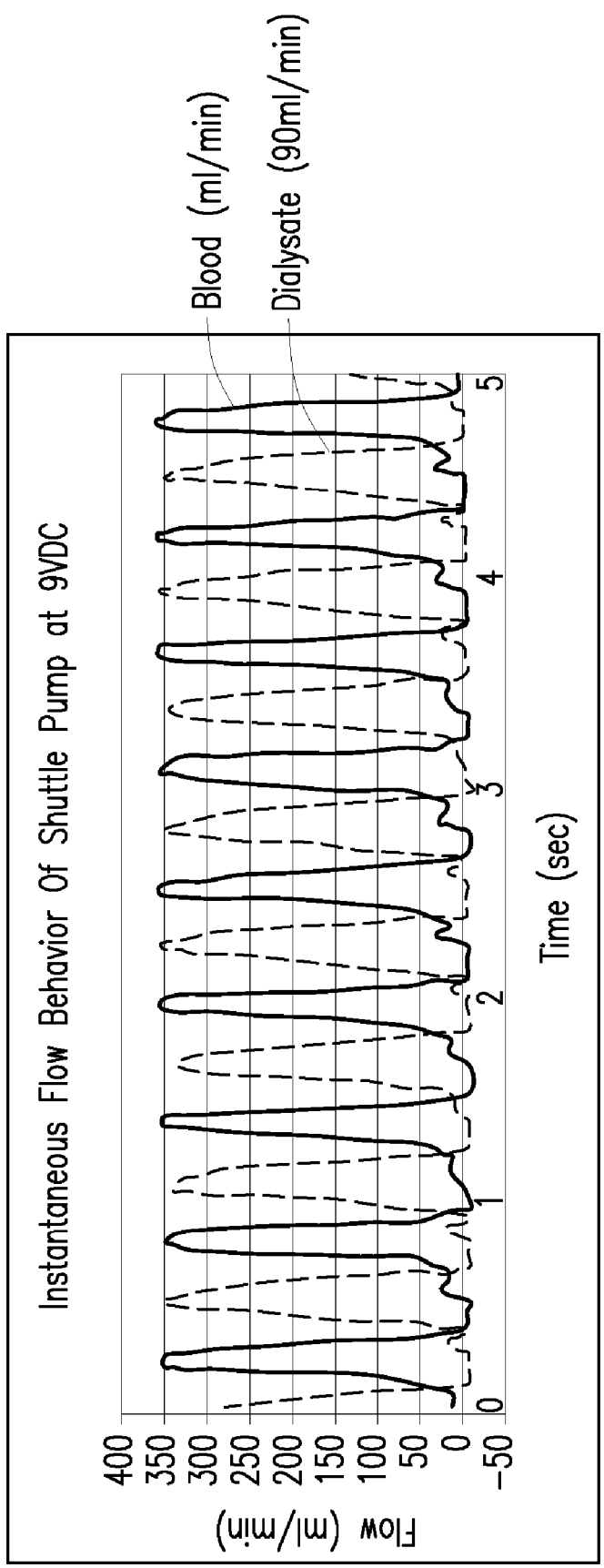
FIG. 22 is a graph depicting the instantaneous flow behavior of an exemplary dual channel pump operating at 9 volts DC.
Figure 23A:
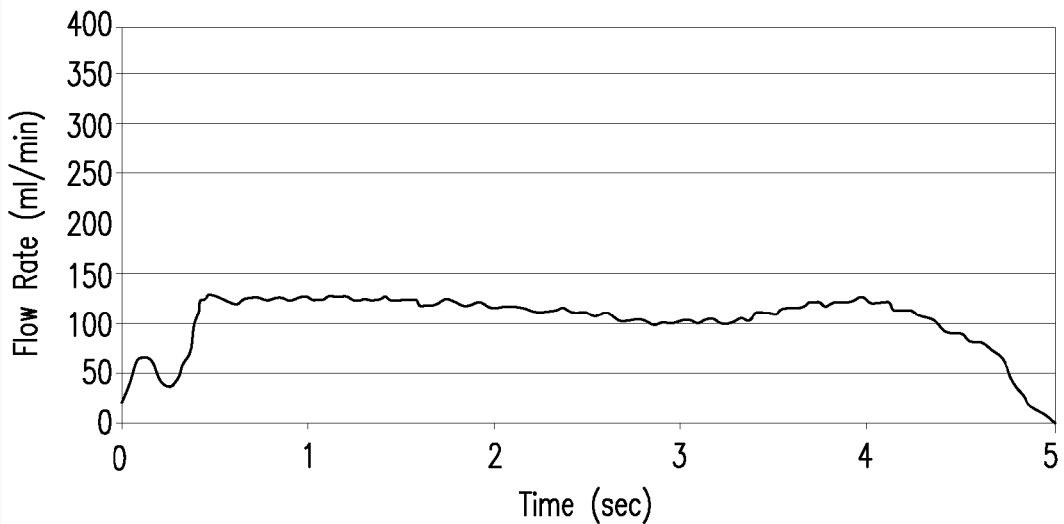
FIGS. 23A and 23B provide a comparison of the instantaneous behavior of different types of roller pumps.
Figure 23B:
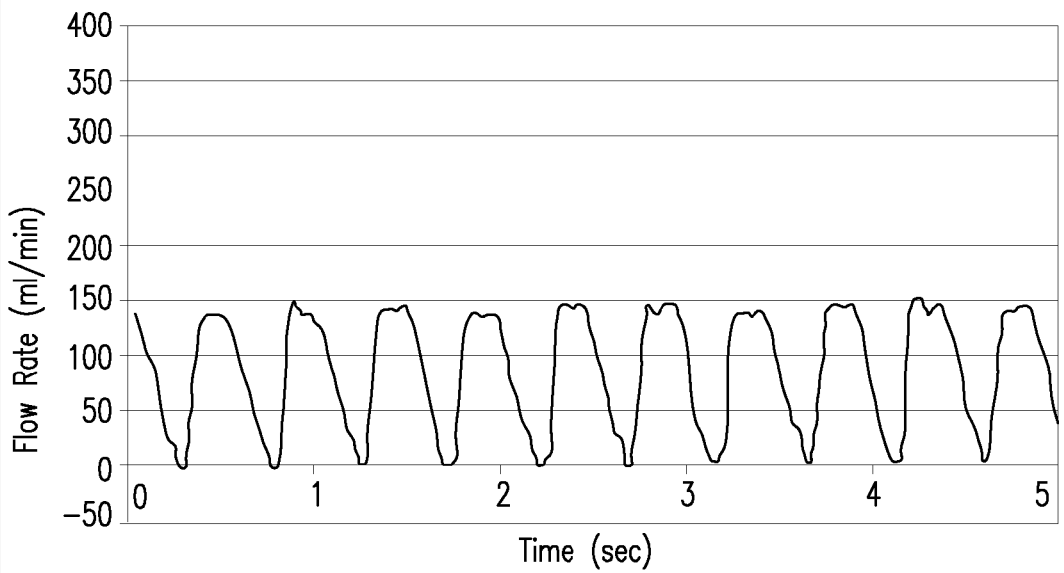

The effects of the pulsatile nature of the different pumps mentioned above are displayed in FIGS. 22 to 24. The exemplary WAK's double channel pump pulsatile pump 1206 provides simultaneous pulsatile flows of both blood and dialysate (FIG. 22). The flows on these two separate channels have a half cycle phase difference.

The exemplary WAK's pump 1206 delivers higher amplitudes as well as much higher pulse frequency than commonly used roller pumps. FIG. 22 shows that the exemplary pump 1200 has a stroke volume of about 0.8 ml, frequency of 110 beats per minute (bpm), and peak instantaneous flow of 350 ml/min running blood at 95 ml/min on average. The corresponding data for the roller pump for the same blood flow are 8 ml, 13 bpm, and 120 ml/min, respectively (see FIG. 23A).

Similarly, the corresponding data for the CRRT roller pump are 0.7 ml, 125 bpm, and 140 ml/min, respectively. (see FIG. 23B).

Figure 24A:
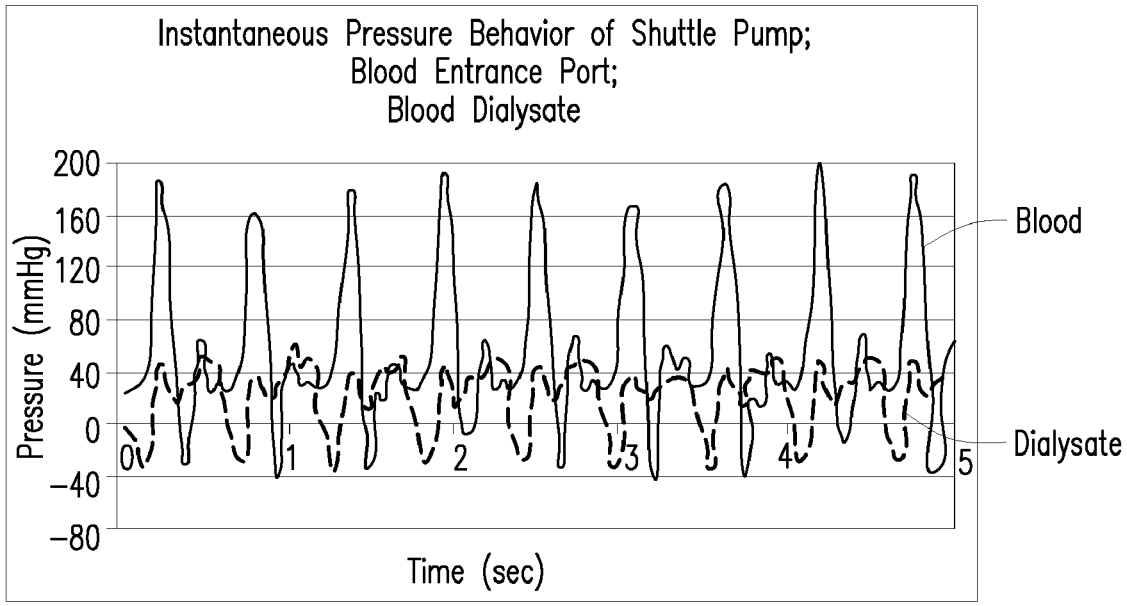
FIGS. 24A and 24B provide a comparison of the instantaneous pressure behavior of and exemplary pump v. other pumps.
Figure 24B:
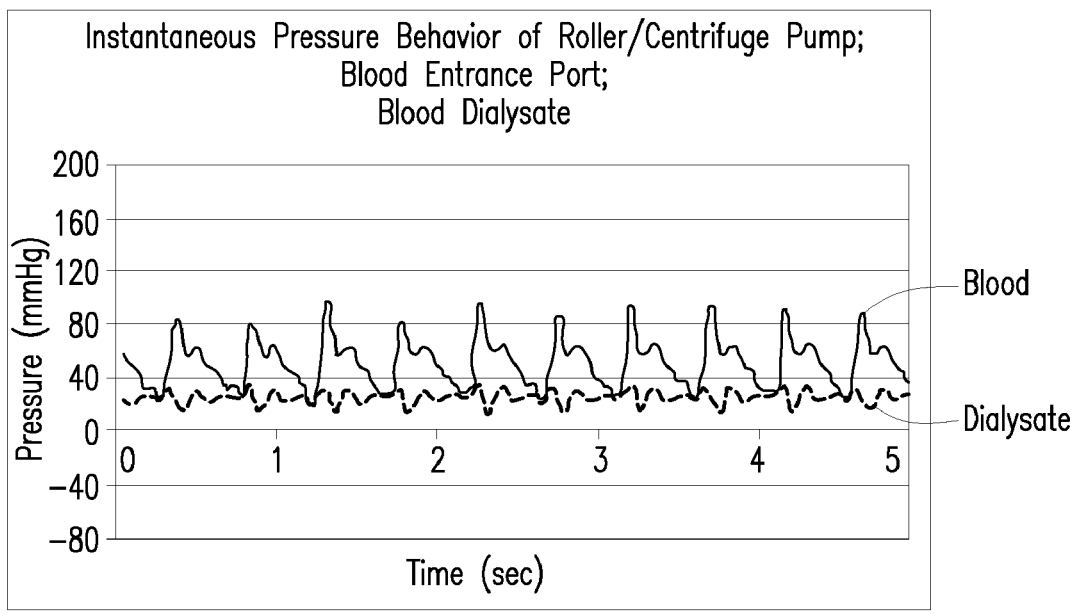
Figure 25A:
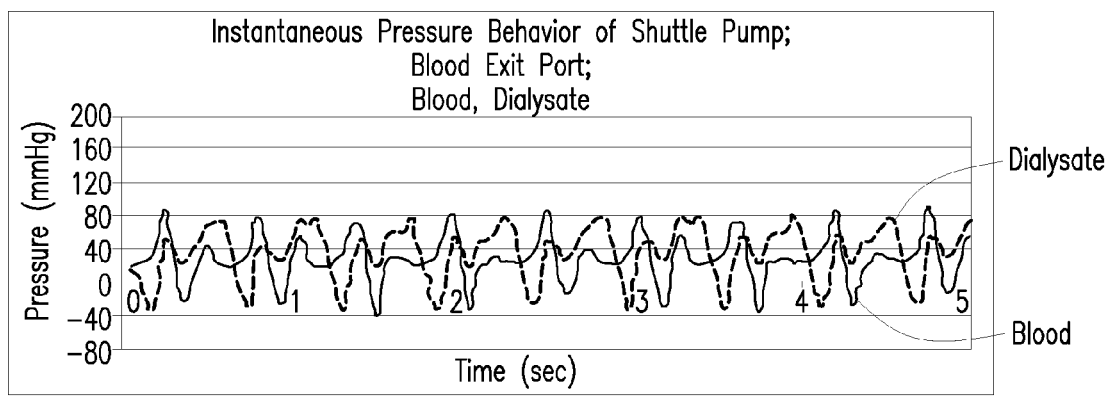
FIGS. 25A and 25B provide a comparison of the instantaneous pressure behavior of an exemplary pump v. a roller/centrifuge pump.
Figure 25B:
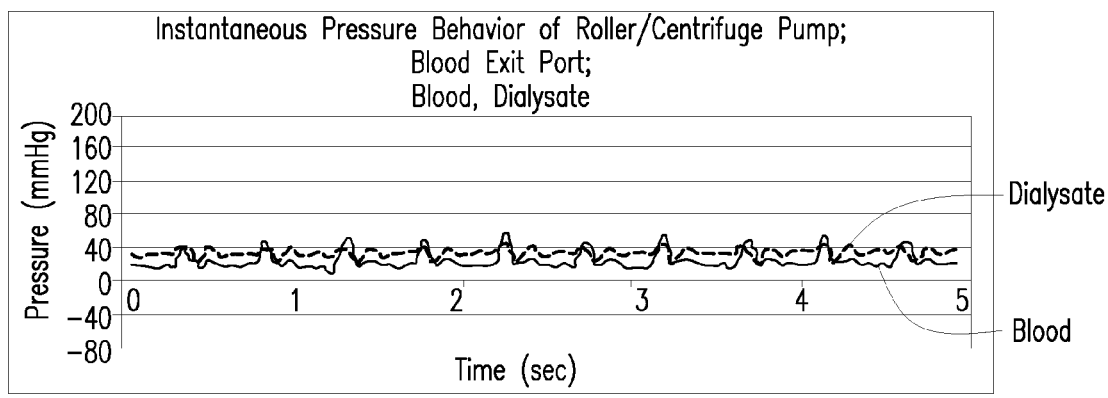

The pressure waves generated by the exemplary WAK pump 1206 allowed for a higher trans-membrane pressure gradient (TMP) than the TMP produced by roller pumps (FIGS. 24A and 24B). The pressure waves in a combination of CRRT-roller-pump moving blood and a centrifugal pump moving dialysate, at the same average flow rates. Analysis of these figures shows that the TMP varies from −10 to +150 mmHg at the blood entrance port (FIG. 24A) and from −50 to +50 mmHg at the blood exit port of the dialyzer with the WAK pump (FIG. 25A top). Corresponding values for combination of roller/centrifugal-pump are 0 to +60 and −10 to +20 mmHg, respectively (FIGS. 24B and 25B).

Solute Clearance by Dialyzers

Another result of the experiments and testing indicated that the pulsating flow of the exemplary dual channel pulsatile pump 1206 produces higher clearances than a continuous, steady, non pulsating flow. This data also shows that the exemplary WAK's palm-sized, battery-operated pump is as effective as the heavier CRRT roller pumps at generating solute clearances with commercial dialyzers, even though the commercial dialyzers are designed for much higher flow rates of blood and dialysate, typically in the 300-500 ml/min range.

Efficiency of Adsorption by the Dialysate Regeneration System

Figure 28A:
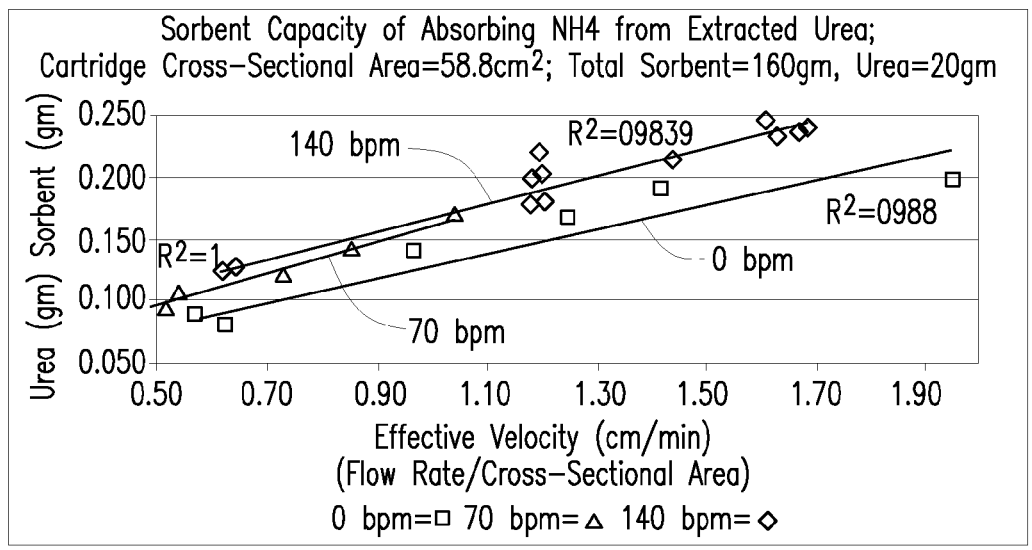
FIG. 28A provides graphic experimental results of the solute clearance using different types of pumps.

Adsorption efficiency using pulsatile flow by both the WAK and the conventional roller pumps versus steady, non-pulsating flow are depicted in FIG. 28A. The amount of Urea removed per gram of sorbent is considerably higher with pulsatile than with non-pulsatile flow. This was an unexpected result.

Figure 28B:
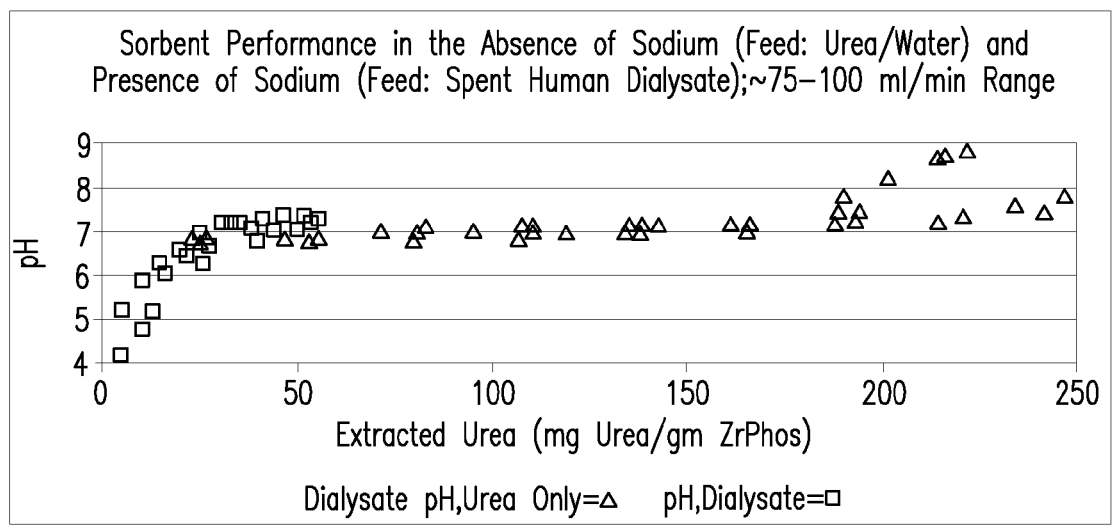
FIG. 28B provides graphic experimental results comparing the sorbent performance of an exemplary wearable artificial kidney with and without optimization of the dialysate pH.

The effects of optimizing the dialysate pH to 7.4 are shown in FIG. 28B. The amount of Urea removed per gram of Zirconium significantly improves when the pH is optimized to 7.4. This was also an unexpected result.

Animal Studies

The results of two animal studies with an a first exemplary WAK using a dialyzer with a smaller surface area that used in animal studies are summarized in Table III and compared to the results obtained with another exemplary WAK 1200.

TABLE III

Animal study results with two different exemplary WAKs
The Wearable Artificial Kidney
8 hours of dialysis, in anesthetized uremic pigs

| Results | | WAK 1200 | Units |
|---|---|---|---|
| Effective urea clearance | 24.1 ± 2.4 | 39.8 ± 2.7 | [mL/min] |
| Effective creatinine clearance | 25.1 ± 2.3 | 40.9 ± 2.3 | [mL/min] |
| Total urea removal | 12.4 ± 2.8 | 15.3 ± 4.4 | [g] |
| Total creatinine removal | 0.9 ± 0.2 | 1.7 ± 0.2 | [g] |
| Total phosphate removal | 0.8 ± 0.2 | N/A | [g] |
| Total potassium removal | 80.5 ± 19.5 | 150.5 ± 16.7 | [mmol] |
| Extrapolated standard Kt/V | 6.9 ± 1.9 | 7.7 ± 0.5 | |

DISCUSSION

Flow/Pressure Behavior

The blood and dialysate that flows within an exemplary WAK or wearable CRRT device each oscillate at a frequency of 1.2-2.4 Hz. This semi-sinusoidal movement provides an alternating stroke volume of about 0.8 ml in each channel. Thus, $$V_m/\pi F = 0.8 \text{ or } V_m = 2.5F \quad (3)$$

where $V_m$ is the maximum temporal volume in a cycle of F Hz. For a blood flow of 95 ml/min and a period of 0.55 sec, $F=1/0.55 \text{ sec}=1.82$ Hz and $V_m=(2.5)(1.82)=4.55 \text{ cm}^3$.

A Hemophan® dialyzer was used with an estimated 1,830 hollow fibers of 100 microns luminal radius, wall thickness of 6.5 microns, and length of 18.5 cm. The estimated blood-flow cross-sectional area and luminal volume are 0.575 $cm^2$ and 10.6 $cm^3$, respectively. Therefore, the blood luminal volume is estimated to increase (4.55)(100)/10.6=42.9% intermittently. For the AN69® dialyzer it would be 4,390 hollow fibers of 120 microns luminal radius, wall thickness of 50 microns, and length of 15 cm; thus the blood-flow cross-sectional area and luminal volume are 1.986 $cm^2$ and 29.8 $cm^3$, respectively. Therefore, the blood luminal volume would increase (4.55)(100)/29.8=15.3% intermittently. Since these capillaries are not elastic and liquids are essentially incompressible, these estimated volume oscillations will almost entirely convert to pressure waves. Using a blood kinematic viscosity of $v=0.03 \text{ cm}^2/\text{sec}$, the corresponding Womeresley number $r(2\pi F/v)^{1/2}$ is 0.195 and 0.235 for Hemophan® (r=0.010 cm) and AN69® (r=0.012 cm) dialyzer, respectively. Since the temporal luminal volume changes considerably and the Womeresley number is not negligible, Poiseuille's law cannot be used in an exemplary WAK. This, is in contrast to currently used large scale dialysis machines where the flow in the dialyzer is parabolic and thus in a steady state. Therefore, Poiseuille's law is considered applicable in conventional machines, but is not applicable to an exemplary WAK.

The exemplary WAK pumps simultaneous pulsatile flows of blood and dialysate (FIG. 22). These two flows have a half cycle phase difference allowing for a push-pull mechanism across the dialyzer membrane and on the surface of the sorbent particles. The blood flow waves generated by the exemplary dual pulsatile pump have higher amplitudes and frequencies than the blood flow waves generated by roller pumps. This is conducive to the considerable differences in the magnitude and direction of the TMP's along the dialyzer fibers, and radically changes the clearances and mass transfer between blood and dialysate. It appears that the push pull mechanism, produced by an exemplary dual channel pulsatile pump across the membrane, may significantly improve the performance of a dialyzer.

The pressure waves generated by the exemplary dual channel pulsatile pump show a different and unique pattern that is completely different from the pressure and TMP patterns seen in traditional dialysis machines. Through our experimentation it was found that there is a pattern of pulsating changes of the TMP (trans-membrane pressure) between blood and dialysate and the time traces. Conversely, this pulsating change behavior is absent in current dialysis machines where TMP is time-independent. Also, we note that the pivots (where blood and dialysate pressure lines cross, TMP=0) are shifted considerably to the right with an exemplary pulsatile flow (i.e. convection from blood to dialysate dominates).

Solute Clearance by Dialyzers

Figure 26A:
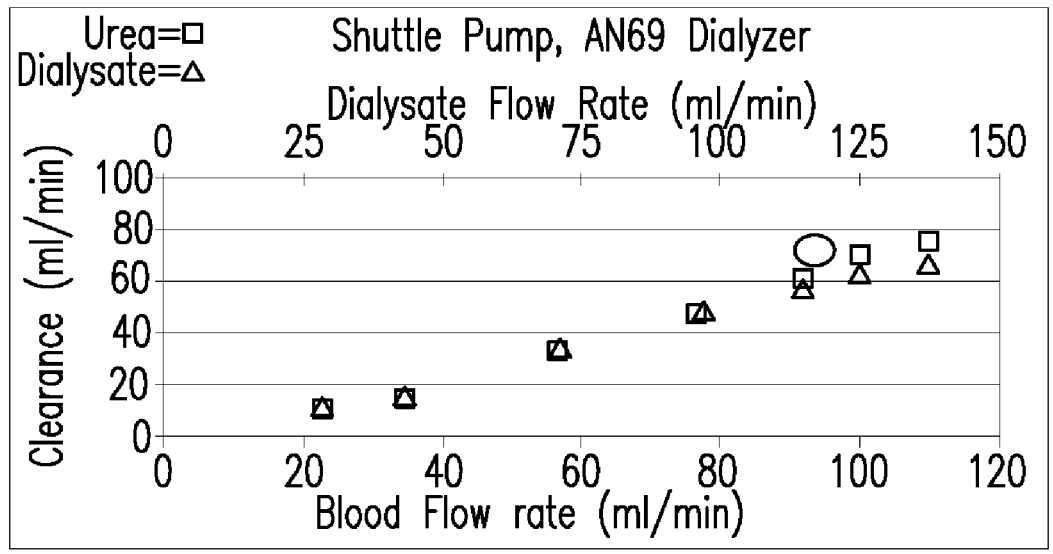
FIGS. 26A and 26B provide experimental results of the solute clearance using different types of pumps.
Figure 26B:
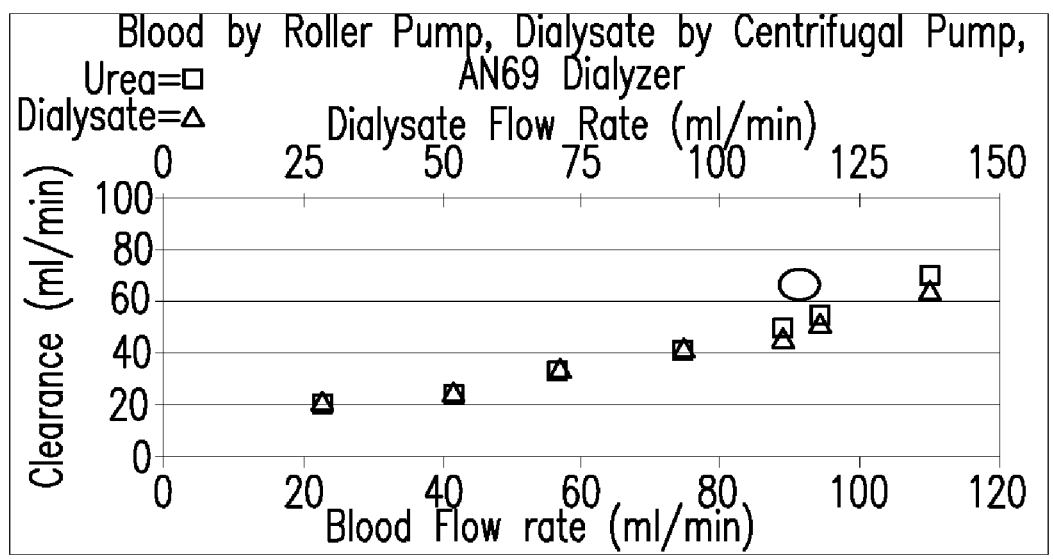
Figure 27A:
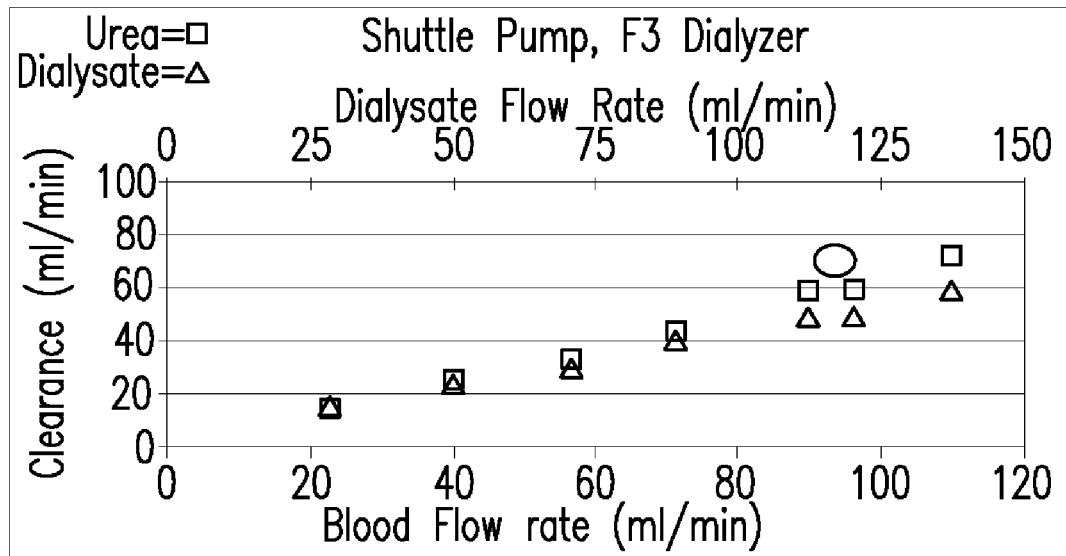
FIGS. 27A and 27B provide experimental results of the solute clearance using different types of pumps.
Figure 27B:
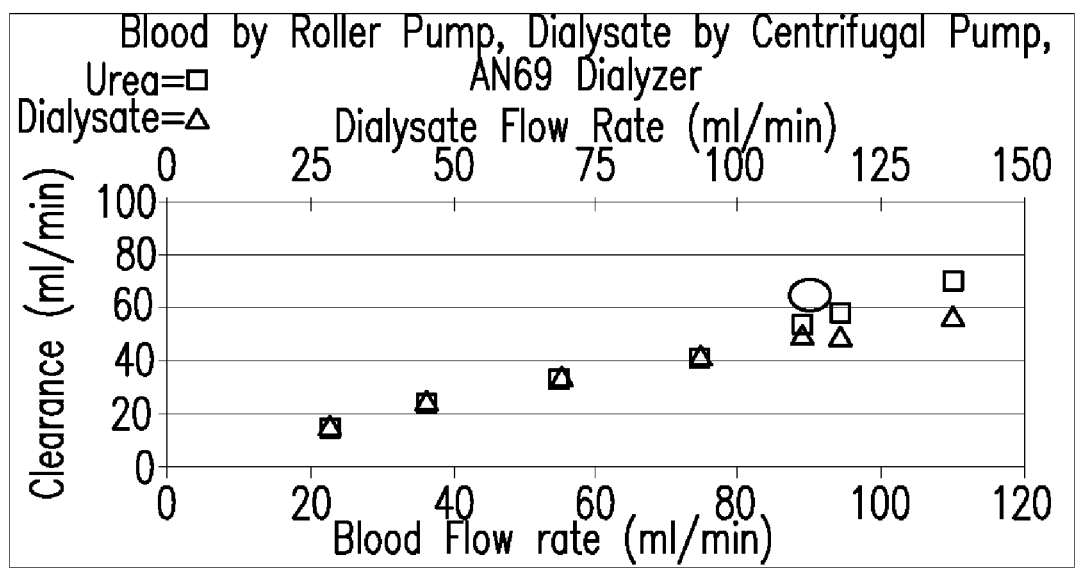

FIGS. 26A and 26B shows that a pulsating flow generated by either the WAK or the conventional roller pumps produces higher clearances than steady flow. FIGS. 27 and 28 demonstrate that an exemplary WAK pump's clearance values are comparable to those produced by roller pumps at the same average flow rates. The former shows results from an AN69 dialyzer, the latter an F3® dialyzer.

Yet, even though an exemplary dual channel pulsatile pump delivers as effective solute clearances as current roller pumps, it operates efficiently with a small 9-Volt battery, while the conventional roller pumps require connection to an electrical outlet that provides 110 or 220 Volts. Furthermore, an exemplary dual channel pulsatile pump can weighs between 300 and 450 grams, while the conventional roller pumps weigh 8 to 12 times more.

Mass Transfer Behavior

Because of the inherent fluctuations of pulsatile flow, any mass transfer process in this system should be considered an unsteady-state. This means, instead of using the customary Fick's first law, $$N = -D\frac{dC}{dr}, \quad (4)$$

one should use Fick's second law, simplified form of which is:

$$-\left(\frac{\partial N}{\partial r}\right) = \left(\frac{\partial C}{\partial t}\right) = D\frac{\partial\left(\frac{\partial C}{\partial r}\right)}{\partial r}$$

for cylindrical geometries such as a hollow fiber, and, $$= D\left[\frac{1}{r^2}\frac{\left(r^2\frac{\partial C}{\partial r}\right)}{\partial r}\right], \quad (5)$$

for spherical geometries such as in sorbent particles.

In these equations, d and ∂ are the simple and partial differentiation symbols respectively, N the mass flux [mass/area/time], D the diffusivity coefficient [square length/time], C the concentration [mass/volume], and r the (radial) diffusion distance [length]. Fick's second law encompasses transient-convective-concentration variations. D is independent of ambient or transient pressure in a liquid system but it is dependent on the porous structure of the powders/granules in sorbent beds. The first part of Equation (5) is a natural starting point for theoretical analysis of a hollow-fiber dialyzer, the second part is for sorbent powders and granules in the dialysate regeneration system. The sorbent beds however, pose a more complicated mass transport due to ion exchange, permeation and leaching; thus they are designed empirically.

Dialyzer Behavior

Solute Clearance: There appears to be an increase in dialyzer mass transfer with pulsatile flow. The reasons for an increase of mass transfer increase have been suggested to be greater fluid energy (i.e., greater mean pressure), enhanced convective and diffusive mass transfer, and avoidance of molecular channeling and membrane layering. It is thought that a negative pressure gradient between dialysate ports enhances ultrafiltration.

Ultrafiltration: Charts commonly generated by manufacturers of dialyzers show Equations (1) and (2) without including the effects of convection due to ultrafiltration. It is estimated that such effects by continuous-flow convective mass transfer to be at least 3%, as follows.

$$\text{Clearance} = \text{Clearance at zero } UF + 0.46 \times UF \quad (6)$$

In a previous animal study that we performed with a first test version of the exemplary WAK, the average clearance and ultrafiltration were 24.6 and 1.67 ml/min (100 ml/hr), respectively. Therefore, UF=1.67 ml/min and 0.46×UF=0.768 ml/min, which is 0.768/24.6=0.031 or 3.1% of Clearance.

This would be true if there was only continuous-flow convection. However, a much higher percentage of convective mass transfer can be expected because of the pulsatile nature of the flow. Intermittent changes of TMP gradient direction along the dialyzer, suggest that an exemplary CRRT device may in fact perform hemodiafiltration since these changes would definitely result in bidirectional convective transit of water and solutes across the membranes.

Efficiency of Adsorption in Sorbents

An exemplary sorbent system used zirconium-phosphate cation-exchange structures containing zirconium, phosphorus, oxygen, nitrogen, and hydrogen, as well as an immobilized Urease/Alumina powder to break down Urea. Using various amounts of immobilized Urease (mostly 35-80 micron, 1.22 gm/ml loose), and zirconium phosphate (mostly 25-45 microns, 1.22 gm/ml loose) the amounts of sorbent used until saturation reached were measured. Using a non-pulsating or a pulsatile (WAK pump) flow, an average effective velocity (flow rate divided by cross-sectional area) is the best parameter to correlate with amounts of Urea extracted per fixed amount of sorbent. FIG. 28B, shows that the pulsatile flow increases the amount of Urea extracted per gram of zirconium phosphate.

We found that when the pH of the dialysate was optimized to 7.4, the result was increased sorbent capacity. This might be explained by adsorption of large amounts of sodium and early-stage replacement/release of $H^+$ by $Na^+$. This would explain early-stage lower adsorption with a lower pH, since acidity might have considerably lowered the adsorption of Ammonia.

Animal Studies

The results of the initial animal studies with a first embodiment of the WAK are summarized in Table 2 and compared to the results obtained with a second exemplary embodiment of the WAK. The Creatinine Clearance improved from 25.1±2.3 to 40.9±2.3 ml/min and the Urea Clearance from 24.1±2.4 to 39.8±2.7 ml/min. The extrapolated weekly kt/v of 6.9±1.9 with the first exemplary WAK rose to 7.7±0.5 with the second exemplary WAK.

This clearance much higher than conventional values from conventional dialysis machines of around 2, and even higher than a reported value of close to 6 for quotidian dialysis. Therefore, the second exemplary WAK qualifies to be on Gotch's straight line of std (Kt/V)=8×sp(Kt/V).

Based on the above discussed experiments and tests, it has been found, rather than hypothesized, that pulsatile flow is superior to steady or continuous flow in generating mass transfer of solutes and clearances. An exemplary WAK's dual channel pulsatile pump generates higher peak blood flows and similar clearances to those of current pumps which are too heavy, energy inefficient, and cumbersome to be part of a wearable device. In contrast, an exemplary WAK pump is light and its small size dimensions and geometry (see exemplary dimensions in FIGS. 14 and 15) allows wearability. The changes in TMP during the pulsations of an exemplary dual channel pulsatile pump along with the pulsations' higher amplitude generate superior rates of mass transfer, mostly by convection. Thus, exemplary WAKs deliver hemodiafiltration and not purely hemodialysis. The half cycle difference between the blood and dialysate pulsations, the magnitude, and the frequency of TMP changes created by an exemplary dual channel pulsatile pump generate a "push-pull" flow through the dialyzer membrane. The exemplary dual channel pump's pulsatile flow improves the superficial velocity of the dialysate that is in contact with the sorbent, further improving the amounts of solutes adsorbed by the adsorbents. A dialysate pH that is maintained at 7.4 improves sorbent efficiency over a non-maintained dialysate pH. A high flux membrane and larger dialyzer surface, improves the exemplary WAK's performance without increasing bulk or weight. The results further indicate that embodiments of the present invention may be the device of choice to optimize the care of ESRD patients, supplying 168 hours a week of high clearance dialysis. It would also obviate the need for and simplify the logistical problems of daily present day intermittent dialysis, hopefully reduce costs, improve quality of life, and reduce mortality in ESRD patients.

Many variations and embodiments of the above-described invention are possible. Although only certain embodiments of the invention have been illustrated in the accompanying drawings and described in the foregoing Detailed Description, it will be understood that the invention is not limited to the embodiments disclosed, but is capable of additional rearrangements, modifications and substitutions without departing from the invention as set forth and defined by the following claims. Accordingly, it should be understood that the scope of the present invention encompasses all such arrangements and is solely limited by the claims as follows:

What is claimed is:

1. A completely wearable artificial kidney (WAK) device comprising:
    a blood circuit;
    a dialysate circuit;
    a dual channel pulsatile pump comprising:
    a first channel for pumping the blood through said blood circuit and a second channel for pumping dialysate through said dialysate circuit; each of said first channel and said second channel comprising:
    a peristaltic tube that is compressible, said peristaltic tube having an input end and an output end;
    an input valve at the input end, said input valve comprising an input o-ring, an input ball adapted to seat against said input o-ring to stop fluid back flow through said input valve and an input spring member adapted to position said input ball against said input o-ring when the peristaltic tube is being compressed, said input spring member further adapted to allow the input ball to move away from said input o-ring and allow forward fluid flow through said input valve when said peristaltic tube decompresses, said input spring member comprises:
        an outer ring having a first diameter;
        an inner ring having a second diameter being smaller than the first diameter; and
        at least two spokes extending radially from the inner ring to the outer ring;
        the inner ring being adapted to move laterally with respect to a plane extending perpendicular to a center axis of the outer ring; and
    an output valve at said output end, said output valve comprising an output o-ring, an output ball adapted to seat against said output o-ring to stop fluid back flow through said output valve and an output spring member adapted to position said output ball against said output o-ring when the peristaltic tube is being decompressed, said output spring member further adapted to allow the output ball to move away from said output o-ring and allow forward fluid flow through said output valve when said peristaltic tube is being compressed; and
    a single electric motor and transmission that alternately compresses and decompress the peristaltic tube in said first channel and said peristaltic tube in said second channel; said dialysate circuit, said blood circuit, and said WAK adapted to be completely worn by said user.

2. The completely wearable artificial kidney (WAK) device of claim 1, wherein said dual channel pulsatile pump is adapted to provide a blood flow rate through said blood circuit of between 15 and 100 ml/min pulsatile.

3. The completely wearable artificial kidney (WAK) device of claim 1, wherein said dual channel pulsatile pump is configured to provide alternating pulses in the first and the second channels that are 180 degrees out of phase.

4. The completely wearable artificial kidney (WAK) device of claim 1, wherein said dual channel pulsatile pump is configured to pump from 0 to 350 ml/min of blood in said blood circuit.

5. The completely wearable artificial kidney (WAK) device of claim 1, wherein said dual channel pulsatile pump is configured to pump from 0 to 350 ml/min of and dialysate in the dialysate circuit.

6. A completely wearable artificial kidney (WAK) device comprising:
    a blood circuit;
    a dialysate circuit;
    a dialyzer connected to both the blood circuit and the dialysate circuit, the dialyzer comprising a blood circuit input, a blood circuit output, a dialysate circuit input and a dialysate circuit output;
    a dual channel pulsatile pump comprising:
    a first channel for pumping blood through said blood circuit and a second channel for pumping dialysate through said dialysate circuit, wherein said first channel comprises:
    a peristaltic tube that is compressible, said peristaltic tube having an input end and an output end;
    an input valve at the input end, said input valve comprising an input ball seat, an input ball adapted to seat against said input ball seat to stop fluid back flow through said input valve and an input spring member comprising an outer ring, a concentric inner ring and at least two spokes extending radially between the outer ring and the concentric inner ring; the input spring member being placed and adapted to position the input ball against said input ball seat when the peristaltic tube is being compressed, said input spring member further adapted to allow the input ball to move away from said input ball seat thereby allowing forward fluid flow through said input valve when said peristaltic tube is being decompressed; and
    an output valve at said output end, said output valve comprising an output ball seat, an output ball adapted to seat against said output ball seat to stop fluid back flow through said output valve and an output spring member adapted to position the output ball against said output ball seat when the peristaltic tube is being decompressed, said output spring member further adapted to allow the output ball to move away from said output ball seat thereby allowing forward fluid flow through said output valve when said peristaltic tube is being compressed;
    said first channel and said second channel providing pump cycles that are out of phase, whereby the combination of the dialyzer and the dual channel pulsatile pump produce a pressure differential that varies periodically from about −10 to about +150 mmHg between the blood circuit input and the dialysate circuit input.

7. The completely wearable artificial kidney (WAK) device of claim 6, wherein the first and second pump cycles are configured to be 180 degrees out of phase.

8. The completely wearable artificial kidney (WAK) device of claim 6, wherein the blood and dialysate pass through the dialyzer in opposing directions.

9. The completely wearable artificial kidney (WAK) device of claim 6, further comprising a pH control system within the wearable artificial kidney, the pH control system adapted to adjust the pH of the dialysate toward a predetermined pH.

10. The completely wearable artificial kidney (WAK) device of claim 6, whereby the combination of the dialyzer and dual pulsatile pump are configured to perform hemodiafiltration and not purely hemodialysis.

* * * * *